US008921538B2

(12) United States Patent
Puthigae et al.

(10) Patent No.: US 8,921,538 B2
(45) Date of Patent: Dec. 30, 2014

(54) CONTROL OF GENE EXPRESSION IN PLANTS

(75) Inventors: Sathish Puthigae, Auckland (NZ);
Jonathan Robert Phillips, Chesterfield, MO (US); Nimali Piyushika Withana, Carlton (AU); Claudia Jeannette Smith-Espinoza, Chesterfield, MO (US); Catherine Jane Bryant, Auckland (NZ); Shivendra Bajaj, Auckland (NZ); Kerry Robert Templeton, Auckland (NZ)

(73) Assignee: Vialactia Biosciences (NZ) Limited, Auckland (NZ)

( * ) Notice: Subject to any disclaimer, the term of this patent is extended or adjusted under 35 U.S.C. 154(b) by 530 days.

(21) Appl. No.: 13/262,535

(22) PCT Filed: Mar. 26, 2010

(86) PCT No.: PCT/NZ2010/000056
§ 371 (c)(1),
(2), (4) Date: Dec. 12, 2011

(87) PCT Pub. No.: WO2010/114395
PCT Pub. Date: Oct. 7, 2010

(65) Prior Publication Data
US 2012/0084880 A1 Apr. 5, 2012

Related U.S. Application Data

(60) Provisional application No. 61/165,776, filed on Apr. 1, 2009.

(51) Int. Cl.
C07H 21/04 (2006.01)
C12N 15/82 (2006.01)
C12N 15/87 (2006.01)
C12N 15/00 (2006.01)
C12N 5/10 (2006.01)

(52) U.S. Cl.
CPC .......... *C12N 15/823* (2013.01); *C12N 15/8227* (2013.01); *C12N 15/8226* (2013.01); *C12N 15/8225* (2013.01)
USPC ....... 536/24.1; 800/278; 800/298; 435/320.1; 435/419; 435/468

(58) Field of Classification Search
None
See application file for complete search history.

(56) References Cited

U.S. PATENT DOCUMENTS

| 4,795,855 | A | 1/1989 | Fillatti et al. |
|---|---|---|---|
| 5,004,863 | A | 4/1991 | Umbeck |
| 5,159,135 | A | 10/1992 | Umbeck |
| 5,177,010 | A | 1/1993 | Goldman et al. |
| 5,187,073 | A | 2/1993 | Goldman et al. |
| 5,188,958 | A | 2/1993 | Moloney et al. |
| 5,352,605 | A | 10/1994 | Fraley et al. |
| 5,364,780 | A | 11/1994 | Hershey et al. |
| 5,416,011 | A | 5/1995 | Hinchee et al. |
| 5,463,174 | A | 10/1995 | Moloney et al. |
| 5,510,474 | A | 4/1996 | Quail et al. |
| 5,563,055 | A | 10/1996 | Townsend et al. |
| 5,569,834 | A | 10/1996 | Hinchee et al. |
| 5,591,616 | A | 1/1997 | Hiei et al. |
| 5,750,871 | A | 5/1998 | Moloney et al. |
| 5,792,935 | A | 8/1998 | Arntzen et al. |
| 5,824,877 | A | 10/1998 | Hinchee et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 7,365,185 | B2 | 4/2008 | Boukharov et al. |
| 7,408,052 | B2 | 8/2008 | Cheikh et al. |
| 7,491,806 | B2 | 2/2009 | Conner et al. |
| 2003/0046732 | A1 | 3/2003 | Kinnersley et al. |
| 2004/0031072 | A1 | 2/2004 | La Rosa et al. |
| 2004/0034888 | A1 | 2/2004 | Liu et al. |
| 2004/0123343 | A1 | 6/2004 | La Rosa et al. |
| 2004/0172684 | A1 | 9/2004 | Kovalic et al. |
| 2004/0214272 | A1 | 10/2004 | La Rosa et al. |
| 2004/0216190 | A1 | 10/2004 | Kovalic |
| 2005/0108791 | A1 | 5/2005 | Edgerton |
| 2006/0123505 | A1 | 6/2006 | Kikuchi et al. |
| 2006/0179511 | A1 | 8/2006 | Chomet et al. |

(Continued)

FOREIGN PATENT DOCUMENTS

WO 01/04285 1/2001
WO 02/00894 3/2002

(Continued)

OTHER PUBLICATIONS

Dolferus_Plant Phys_105_1075_1994.*
Donald_EMBO J_9_1717_1990.*
Kim_Plant Mol Biol_24_105_1994.*
Potenza_In Vitro Cell Dev Biol Plant_40_1_2004.*

(Continued)

*Primary Examiner* — Medina A Ibrahim
*Assistant Examiner* — Russell Boggs
(74) *Attorney, Agent, or Firm* — Lathrop & Gage LLP

(57) ABSTRACT

The invention provides the isolated promoter polynucleotide sequence of SEQ ID NO: 1 from perennial ryegrass (*Lolium perenne* L.), and fragments and variants thereof. The invention also provides constructs, plant cells and plant genetically modified to contain the promoter polynucleotide. The invention also provides methods for producing plants with altered gene expression and traits via genetic transformation of plants with the promoter polynucleotide.

12 Claims, 11 Drawing Sheets

(56) References Cited

U.S. PATENT DOCUMENTS

| | | | |
|---|---|---|---|
| 2006/0236419 | A1 | 10/2006 | La Rosa et al. |
| 2007/0020621 | A1 | 1/2007 | Boukharov et al. |
| 2007/0044171 | A1 | 2/2007 | Kovalic et al. |
| 2007/0067865 | A1 | 3/2007 | Kovalic et al. |
| 2007/0294782 | A1 | 12/2007 | Abad et al. |
| 2008/0301839 | A1 | 12/2008 | Ravanello |
| 2010/0242134 | A1 | 9/2010 | Puthigae et al. |
| 2010/0293664 | A1 | 11/2010 | Puthigae et al. |
| 2011/0179517 | A1 | 7/2011 | Puthigae et al. |
| 2011/0185452 | A1 | 7/2011 | Puthigae et al. |
| 2011/0209250 | A1 | 8/2011 | Puthigae et al. |
| 2011/0302670 | A1 | 12/2011 | Puthigae et al. |
| 2011/0302674 | A1 | 12/2011 | Puthigae et al. |

FOREIGN PATENT DOCUMENTS

| | | |
|---|---|---|
| WO | 02/50294 | 6/2002 |
| WO | 2004/058963 | 7/2004 |
| WO | 2004/113536 | 12/2004 |
| WO | 2005/123919 | 12/2004 |
| WO | 2007/027866 | 3/2007 |
| WO | 2007/044043 | 4/2007 |
| WO | 2007/049275 | 5/2007 |
| WO | 2007/078286 | 7/2007 |
| WO | 2008/121008 | 10/2008 |

OTHER PUBLICATIONS

Search Report and Written Opinion, dated Jul. 15, 2010, corresponding to International Application No. PCT/NZ2010/000056 (filed Mar. 26, 2010), parent of the present application, 11 pp.

GenBank Accession No. DT709751, Sep. 12, 2005, 1 pg.

Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.

Alam et al. (1999) "Transgenic Insect-Resistant Maintainer Line (IR68899B) for Improvement of Hybrid Rice," Plant Cell Reports 18:572-575.

Altschul et al. (1997) "Gapped BLAST and PSI-BLAST: a New Generation of Protein Database Search Programs," Nucleic Acids Res 25(17):3389-3402.

Bairoch et al. (1994) "PROSITE: Recent Developments," Nuc. Acids Res. 22(17):3583-3589.

Bajaj et al. (2006) "A High Throughput *Agrobacterium tumefaciens*-Mediated Transformation Method for Functional Genomics of Perennial Ryegrass (*Lolium perenne* L.)," Plant Cell Rep. 25:651-659.

Baxevanis, A.D. (2001) "The Molecular Biology Database Collection: an updated compilation of biological database resources," Nucleic Acids Research 29(1):1-10.

Birch, R.G. (1997) "Plant Transformation: Problems and Strategies for Practical Application," Ann Rev Plant Phys Plant Mol Biol 48:297-326.

Bolton et al. (1962) "A General Method for the Isolation of RNA Complementary to DNA," PNAS 48:1390-1397.

Bowie et al. (1990) "Deciphering the Message in Protein Sequences: Tolerance to Amino Acid Substitutions," Science 247:1306-1310.

De Carvalho Niebel et al. (1995) "Post Transcriptional Cosuppression of β-1,3-Glucanase Genes Does Not Affect Accumulation of Transgene Nuclear mRNA," Plant Cell 7:347-358.

Degenhardt et al. (1994) "Two 10-bp Regions Are Critical for Phytochrome Regulation of a *Lemna gibba* Lhcb Gene Promoter," Plant Cell 6(8):1123-1134.

Falquet et al. (2002) "The PROSITE Database, Its Status in 2002," Nucleic Acids Res. 30(1):235-238.

Feng and Doolittle (1987) "Progressive Sequence Alignment as a Prerequisite to Correct Phylogenetic Trees," J. Mol. Evol. 25:351-360.

Frohman, M.A. (1993) "Rapid Amplification of Complementary DNA Ends for Generation of Full-Length Complementary DNAs: Thermal RACE," Methods Enzymol. 218:340-356.

Ghosh D. (2000) "Object-Oriented Transcription Factors Database (ooTFD)," Nucleic Acids Research 28:308-310.

Giesen et al. (1998) "A Formula for Thermal Stability (Tm) Prediction of PNA/DNA Duplexes," Nucleic Acids Res. 26(21):5004-5006.

Hashimoto et al. (2004) "5'-End SAGE for the Analysis of Transcriptional Start Sites," Nature Biotechnology 22(9):1146-1149.

Herrera-Estrella et al. (1983) "Expression of Chimaeric Genes Transferred Into Plant Cells Using a Ti-Plasmid-Derived Vector," Nature 303:209-213.

Hofmann et al. (1999) "The PROSITE Database, Its Status in 1999," Nucleic Acids Res. 27(1):215-219.

Horsch et al. (1985) "A Simple and General Method for Transferring Genes into Plants," Science 227:1229-1231 with correction of authorship.

Huang, X. (1994) "On Global Sequence Alignment. Computer Applications in the Biosciences," 10(3):227-235.

Jefferson et al. (1987) "GUS Fusions: ,B-glucuronidase as a Sensitive and Versatile Gene Fusion Marker in Higher Plants," EMBO 6:3901-3907.

Jones et al. (1998) "The Effect of Chimeric Transgene Architecture on Co-Ordinated Gene Silencing," Planta 204:499-505.

Krens et al. (1997) "Transgenic Caraway, *Carum carvi* L.: a Model Species for Metabolic Engineering," Plant Cell Reports 17:39-43.

Kumar et al. (1996) "Potato Plants Expressing Antisense and Sense S-Adenosylmethionine Decarboxylase (SAMDC) Transgenes Show Altered Levels of Polyamines and Ethylene: Antisense Plants Display Abnormal Phenotypes," The Plant J. 9(2):147-158.

Lee et al. (2010) "Validation of Reference Genes for Quantitative RT-PCR Studies of Gene Expression in Perennial Ryegrass (*Lolium perenne* L.)," BMC Molecular Biology 11:8, 14 pp.

Li et al. (1996) "Genetic Transformation of Cassava (*Manihot esculenta* Crantz)," Nature Biotechnology 14:736-740.

Llave et al. (2002) "Cleavage of Scarecrow-like mRNA Targets Directed by a Class of *Arabidopsis* miRNA," Science 297:2053-2056.

McIntyre et al. (1996) "Strategies for the Suppression of Peroxidase Gene Expression in Tobacco. I. Designing efficient ribozymes," Transgenic Research 5:257-262.

Michelmore et al. (1987) "Transformation of Lettuce (*Lactuca sativa*) Mediated by *Agrobacterium tumefaciens*," Plant Cell Reports 6:439-442.

Napoli et al. (1990) "Introduction of a Chimeric Chalcone Synthase Gene into Petunia Results in Reversible Co-Suppression of Homologous Genes in trans," The Plant Cell 2:279-289.

Needleman et al. (1970) "A General Method Applicable to the Search for Similarities in the Amino Acid Sequence of Two Proteins," J. Mol. Biol. 48:443-453.

Nielsen et al. (Dec. 6, 1991) "Sequence-Selective Recognition of DNA by Strand Displacement with a Thymine-Substituted Polyamide," Science 254(5037):1497-1500.

Niu et al. (1998) "Transgenic Peppermint (*Mentha* x *piperita* L.) Plants Obtained by Cocultivation with *Agrobacterium tumefaciens*," Plant Cell Reports 17:165-171.

Notredame et al. (2000) "T-Coffee: A Novel Method for Fast and Accurate Multiple Sequence Alignment," J. Mol. Biol. 302:205-217.

Ortiz et al. (1996) "Hygromycin Resistance as an Efficient Selectable Marker for Wheat Stable Transformation," Plant Cell Reports 15:877-881.

Pena et al. (1995) "High Efficiency *Agrobacterium*-Mediated Transformation and Regeneration of Citrus," Plant Science 104:183-191.

Rice et al. (Jun. 2000) EMBOSS: The European Molecular Biology Open Software Suite, Trends in Genetics 16(6):276-277.

Schrott, M. (1995) "Selectable Marker and Reporter Genes," In: Gene Transfer to Plants (Potrykus, T., Spangenberg. Eds) Springer Verlag. Berline, pp. 325-336.

Tatusova et al. (1999) "BLAST 2 Sequences, a New Tool for Comparing Protein and Nucleotide Sequences", FEMS Microbiol Lett. 174:247-250.

(56) References Cited

OTHER PUBLICATIONS

Thompson et al. (1994) "CLUSTAL W: Improving the Sensitivity of Progressive Multiple Sequence Alignment Through Sequence Weighting, Position-Specific Gap Penalties and Weight Matrix Choice," Nucleic Acids Research 22:4673-4680.

Triglia et al. (1988) "A Procedure for In Vitro Amplification of DNA Segments That Lie Outside the Boundaries of Known Sequences," Nucleic Acids Res. 16(16):8186.

Wheeler et al. (2001) "Database Resources of the National Center for Biotechnology Information," Nucleic Acids Research 29(1):11-16.

* cited by examiner

```
gtacatagcctccaaacattcttagaggctcgctacaggtattgtaatccgccgttatcggagaag
gggcagtgtgcccggtagatttccggtgaaaataatgtttggaaaaataaagtccagttctgaaac
agagtgccagtattccatgcgaccgcagcagccagcaggtgtacatatacatctcccoctccgccg
tgatttgAcgcgagaaagaggacatccaccagccacactcacacaaacagccccggctagttcccc
cacctttcccttcccttccactccgcatccatctcccatctccggcccattaatatccaccacctc
ctcctcctcctcctcctcctccaagtcgccattactgccgtagacggagctgcgagatagcga
ggagagagat
```

Figure 1

| Site (Length) | Position | Score (Gaps) | Occurrence | Exp Value |
|---|---|---|---|---|
| vgr-CCAAT(12) | 9 | 9 ( 0) | 1 | 1.75e-03 |
| IRS-CS (x)'(7) | 12 | 7 ( 0) | 3 | 3.24e-01 |
| bicoid-CAMLG'(8) | 43 | 8 ( 0) | 1 | 1.22e-02 |
| LF-A2 RS2'(12) | 52 | 9 ( 0) | 1 | 1.75e-03 |
| Myb CS'(6) | 52 | 6 ( 0) | 1 | 5.44e-01 |
| NF-Y-consensus'(13) | 52 | 10 ( 0) | 2 | 2.97e+00 |
| c-Myb CS1(6) | 52 | 6 ( 0) | 1 | 5.44e-01 |
| v-MCS'(6) | 52 | 6 ( 0) | 1 | 5.44e-01 |
| CR CS'(11) | 53 | 8 ( 0) | 1 | 2.57e+00 |
| GAGATA-CS'(6) | 56 | 6 ( 0) | 1 | 6.91e-01 |
| CAC-binding-PBG'(7) | 66 | 7 ( 0) | 1 | 4.77e-02 |
| CSS (2)'(7) | 73 | 7 ( 0) | 1 | 4.77e-02 |
| GR-intron-site-(6) | 73 | 6 ( 0) | 1 | 1.78e-01 |
| C/EBPa-MCSFR(9) | 83 | 8 ( 0) | 1 | 1.22e-02 |
| H4TF-1hist(6) | 84 | 6 ( 0) | 1 | 1.78e-01 |
| Elk-1-CS'(10) | 85 | 10 ( 0) | 1 | 9.26e-02 |
| Elk CS1'(9) | 85 | 9 ( 0) | 1 | 2.40e-02 |
| Ets CS'(9) | 85 | 9 ( 0) | 1 | 9.26e-02 |
| GG-II/GG-I'(6) | 85 | 6 ( 0) | 1 | 1.78e-01 |
| PEA3 CS2'(9) | 85 | 9 ( 0) | 1 | 1.77e-01 |
| SAP-1 CS'(9) | 85 | 9 ( 0) | 1 | 4.75e-02 |
| gamma-IRE CS'(8) | 96 | 6 ( 0) | 3 | 9.57e-01 |
| IRS-CS (x)(7) | 102 | 7 ( 0) | 1 | 3.24e-01 |
| Sp1-1/PU.1 CS(12) | 104 | 9 ( 0) | 1 | 1.96e+00 |
| IL2-NFAT-45(9) | 106 | 9 ( 0) | 1 | 3.04e-03 |
| IRS-CS (x)'(7) | 109 | 7 ( 0) | 2 | 3.24e-01 |
| gamma-IRE CS'(8) | 111 | 6 ( 0) | 2 | 9.57e-01 |
| HN4(9) | 115 | 9 ( 0) | 1 | 3.04e-03 |
| gamma-IRS CS'(8) | 116 | 6 ( 0) | 1 | 9.57e-01 |
| Nkx-3.2 CS(6) | 133 | 6 ( 0) | 1 | 6.91e-01 |
| MT-1.1'(6) | 134 | 6 ( 0) | 1 | 1.78e-01 |
| ONP-undefined-s'(6) | 136 | 6 ( 0) | 1 | 1.78e-01 |
| gamma-IRE CS(8) | 140 | 6 ( 0) | 1 | 9.57e-01 |
| PE-a(7) | 153 | 7 ( 0) | 1 | 4.77e-02 |
| PEA2 RS(7) | 153 | 7 ( 0) | 1 | 4.77e-02 |
| PEBP2 RS(6) | 153 | 6 ( 0) | 1 | 1.78e-01 |
| AP-2-alpha/gamm(9) | 163 | 7 ( 0) | 1 | 8.28e-01 |
| E47 CS'(9) | 166 | 9 ( 0) | 1 | 7.89e-02 |
| E2A CS(7) | 167 | 6 ( 0) | 1 | 3.24e-01 |
| E2A site consen'(7) | 167 | 7 ( 0) | 1 | 2.54e-01 |
| L-PGDS-B-box'(8) | 167 | 8 ( 0) | 1 | 1.22e-02 |
| MyoD-MCK-right '(6) | 168 | 6 ( 0) | 1 | 1.78e-01 |
| AP-2 CS4(10) | 186 | 9 ( 0) | 1 | 1.77e-01 |
| Sp1-cyclin-D2(11) | 187 | 9 ( 0) | 1 | 6.42e-03 |
| AP-2 CS6(8) | 188 | 7 ( 0) | 1 | 5.43e-03 |
| Sp1-HPY(7) | 188 | 7 ( 0) | 1 | 4.77e-02 |
| NF-Y-consensus'(13) | 196 | 10 ( 0) | 1 | 2.97e+00 |
| PR-uterogl.6'(8) | 215 | 9 ( 0) | 1 | 1.22e-02 |
| GR-MT-IIA'(6) | 217 | 6 ( 0) | 1 | 1.78e-01 |
| c-fos SRE half-'(7) | 218 | 7 ( 0) | 1 | 4.77e-02 |
| E1A-F CS'(6) | 220 | 6 ( 0) | 1 | 3.25e-01 |
| HC3(6) | 224 | 6 ( 0) | 2 | 1.78e-01 |
| Sp1-site C'(11) | 230 | 8 ( 0) | 1 | 6.42e-03 |
| Nkx-3.2 CS'(6) | 234 | 6 ( 0) | 1 | 6.91e-01 |
| FOX family CS'(7) | 241 | 7 ( 0) | 1 | 5.44e-01 |
| Forkhead CS(7) | 241 | 7 ( 0) | 1 | 5.44e-01 |
| HNF-5 CS'(7) | 241 | 7 ( 0) | 1 | 1.78e-01 |
| HNF-5 site(7) | 241 | 7 ( 0) | 1 | 1.78e-01 |
| IRS-CS (x)'(7) | 241 | 7 ( 0) | 1 | 3.24e-01 |
| Sp1-complement (7) | 246 | 7 ( 0) | 1 | 4.77e-02 |
| GCF CS'(7) | 248 | 7 ( 0) | 1 | 5.44e-01 |
| CAC-bp-beta-glo'(7) | 262 | 7 ( 0) | 1 | 4.77e-02 |
| Sp1-YR1(6) | 263 | 6 ( 0) | 1 | 1.78e-01 |
| IRF.2(6) | 268 | 6 ( 0) | 1 | 1.78e-01 |
| IRF-2 RS'(8) | 269 | 6 ( 0) | 1 | 1.77e-01 |
| Lyf/Ikaros site'(6) | 269 | 6 ( 0) | 1 | 3.25e-01 |
| JCV-Pnt2'(10) | 271 | 10 ( 0) | 1 | 7.59e-04 |
| alpha-INF.2'(6) | 271 | 6 ( 0) | 2 | 5.44e-01 |
| PU1/Spi1-macros'(9) | 274 | 8 ( 0) | 1 | 1.22e-02 |
| alpha-INF.2'(6) | 276 | 6 ( 0) | 1 | 5.44e-01 |
| COL1A1-B(7) | 296 | 7 ( 0) | 1 | 4.77e-02 |
| PTF1-consensus'(6) | 298 | 6 ( 0) | 1 | 1.78e-01 |

Figure 2

| | | | | |
|---|---|---|---|---|
| GCF_CS(7) | 306 | 7 ( 0) | 1 | 5.44e-01 |
| Isl-1 site'(7) | 311 | 7 ( 0) | 1 | 5.44e-01 |
| N-Oct-3-CS(7) | 312 | 7 ( 0) | 1 | 1.78e-01 |
| HC3(6) | 321 | 6 ( 0) | 1 | 1.78e-01 |
| Egr-1-PDGF-A'(14) | 326 | 11 ( 0) | 6 | 1.26e-04 |
| Egr-1-PDGF-A'(14) | 329 | 14 ( 0) | 5 | 2.94e-06 |
| S1_HS(9) | 329 | 9 ( 0) | 7 | 3.04e-03 |
| Egr-1-PDGF-A'(14) | 332 | 14 ( 0) | 4 | 2.94e-06 |
| S1_HS(9) | 332 | 9 ( 0) | 6 | 3.04e-03 |
| Egr-1-PDGF-A'(14) | 335 | 14 ( 0) | 3 | 2.94e-06 |
| S1_HS(9) | 335 | 9 ( 0) | 5 | 3.04e-03 |
| Egr-1-PDGF-A'(14) | 338 | 14 ( 0) | 2 | 2.94e-06 |
| S1_HS(9) | 338 | 9 ( 0) | 4 | 3.04e-03 |
| Egr-1-PDGF-A'(14) | 341 | 14 ( 0) | 1 | 2.94e-06 |
| S1_HS(9) | 341 | 9 ( 0) | 3 | 3.04e-03 |
| S1_HS(9) | 344 | 9 ( 0) | 2 | 3.04e-03 |
| S1_HS(9) | 347 | 9 ( 0) | 1 | 3.04e-03 |
| WAP_US5(6) | 354 | 6 ( 0) | 1 | 1.78e-01 |
| UPE(6) | 363 | 6 ( 0) | 1 | 5.44e-01 |
| MED-1'(6) | 378 | 6 ( 0) | 1 | 3.25e-01 |
| GAGATA-CS(6) | 387 | 6 ( 0) | 1 | 6.91e-01 |
| NF-E1.6'(6) | 387 | 6 ( 0) | 1 | 1.78e-01 |
| GATA-1-beta-glo(6) | 388 | 6 ( 0) | 1 | 1.78e-01 |
| GATA-1-zeta-glo'(6) | 388 | 6 ( 0) | 1 | 1.78e-01 |
| GATA-1_CS1(6) | 388 | 6 ( 0) | 1 | 5.44e-01 |

Figure 2 Cont.

| Factor or Site Name | Loc.(Str.) | | Signal Sequence | SITE # |
|---|---|---|---|---|
| ANAERO2CONSENSUS | site | 159 (+) | AGCAGC | S000478 |
| ARR1AT | site | 83 (+) | NGATT | S000454 |
| ARR1AT | site | 199 (+) | NGATT | S000454 |
| ARR1AT | site | 46 (-) | NGATT | S000454 |
| ASF1MOTIFCAMV | site | 204 (+) | TGACG | S000024 |
| CAATBOX1 | site | 41 (-) | CAAT | S000028 |
| CACTFTPPCA1 | site | 234 (+) | YACT | S000449 |
| CACTFTPPCA1 | site | 283 (+) | YACT | S000449 |
| CACTFTPPCA1 | site | 366 (+) | YACT | S000449 |
| CACTFTPPCA1 | site | 71 (-) | YACT | S000449 |
| CACTFTPPCA1 | site | 135 (-) | YACT | S000449 |
| CACTFTPPCA1 | site | 141 (-) | YACT | S000449 |
| CURECORECR | site | 1 (+) | GTAC | S000493 |
| CURECORECR | site | 173 (+) | GTAC | S000493 |
| CURECORECR | site | 1 (-) | GTAC | S000493 |
| CURECORECR | site | 173 (-) | GTAC | S000493 |
| DOFCOREZM | site | 115 (+) | AAAG | S000265 |
| DOFCOREZM | site | 213 (+) | AAAG | S000265 |
| DOFCOREZM | site | 268 (-) | AAAG | S000265 |
| DPBFCOREDCDC3 | site | 168 (-) | ACACNNG | S000292 |
| EBOXBNNAPA | site | 168 (+) | CANNTG | S000144 |
| EBOXBNNAPA | site | 168 (-) | CANNTG | S000144 |
| EECCRCAH1 | site | 84 (+) | GANTTNC | S000494 |
| GATABOX | site | 389 (+) | GATA | S000039 |
| GATABOX | site | 56 (-) | GATA | S000039 |
| GATABOX | site | 318 (-) | GATA | S000039 |
| GT1CONSENSUS | site | 94 (+) | GRWAAW | S000198 |
| GT1CONSENSUS | site | 107 (+) | GRWAAW | S000198 |
| GT1CONSENSUS | site | 108 (+) | GRWAAW | S000198 |
| GT1CONSENSUS | site | 85 (-) | GRWAAW | S000198 |
| GT1GMSCAM4 | site | 108 (+) | GAAAAA | S000453 |
| GTGANTG10 | site | 92 (+) | GTGA | S000378 |
| GTGANTG10 | site | 198 (+) | GTGA | S000378 |
| GTGANTG10 | site | 237 (-) | GTGA | S000378 |
| IBOXCORE | site | 55 (-) | GATAA | S000199 |
| MYB2CONSENSUSAT | site | 52 (-) | YAACKG | S000409 |
| MYBCORE | site | 52 (+) | CNGTTR | S000176 |
| MYBCOREATCYCB1 | site | 52 (-) | AACGG | S000502 |
| MYBST1 | site | 318 (-) | GGATA | S000180 |
| MYCCONSENSUSAT | site | 168 (+) | CANNTG | S000407 |
| MYCCONSENSUSAT | site | 168 (-) | CANNTG | S000407 |
| NODCON2GM | site | 214 (-) | CTCTT | S000462 |
| NTBBF1ARROLB | site | 114 (-) | ACTTTA | S000273 |
| OSE2ROOTNODULE | site | 214 (-) | CTCTT | S000468 |
| POLASIG1 | site | 112 (+) | AATAAA | S000080 |
| POLASIG3 | site | 97 (+) | AATAAT | S000088 |
| POLLEN1LELAT52 | site | 211 (+) | AGAAA | S000245 |
| RAV1BAT | site | 168 (-) | CACCTG | S000315 |
| ROOTMOTIFTAPOX1 | site | 316 (-) | ATATT | S000098 |
| SITEIIATCYTC | site | 308 (-) | TGGGCY | S000474 |
| SORLIP1AT | site | 230 (+) | GCCAC | S000482 |
| SORLIP2AT | site | 308 (-) | GGGCC | S000483 |
| TAAAGSTKST1 | site | 114 (+) | TAAAG | S000387 |
| TATABOX3 | site | 313 (-) | TATTAAT | S000110 |
| TATABOX5 | site | 96 (-) | TTATTT | S000203 |
| TATABOX5 | site | 111 (-) | TTATTT | S000203 |
| TATCCAOHVAL21 | site | 318 (+) | TATCCAC | S000416 |
| TATCCAOSAMY | site | 318 (+) | TATCCA | S000403 |
| TATCCAYMOTIFOSRAMY3D | site | 318 (+) | TATCCAY | S000256 |
| UP1ATMSD | site | 308 (+) | GGCCCAWWW | S000471 |
| WBOXATNPR1 | site | 203 (+) | TTGAC | S000390 |
| WRKY71OS | site | 204 (+) | TGAC | S000447 |
| WUSATAg | site | 311 (-) | TTAATGG | S000433 |

Figure 3 gtacatagcctccaaacattcttagaggccgctacaggtattgtaatccgccgttatcgagaagggcagtgtgcccggtagattccggtgaaataa tgtttggaaaataagtccagttctgaaacagagtgccagtattccatgcgaccgcagccagcagcaggtgtaca<u>tata</u>catctcccctccgccgtgat tt<u>gAgc</u>gagaaagaggacatccaccac<u>agccaac</u>act<u>ca</u>ca<u>caa</u>t<u>cag</u>cc<u>g</u>gctagt<u>gcccca</u>c<u>attccct</u>t<u>cct</u>t<u>cc</u>c<u>ttccacc</u>ccgatccatctctccat ctccg<u>cccca</u>tt<u>aa</u>tatccaccacct<u>ggtcctctctcctcgttccccttcctcggccccaagtcg</u>ccatt<u>a</u>ct<u>g</u>cc<u>g</u>tagacg<u>g</u>agctgcgag<u>ataa</u>gc<u>ga</u>g<u>gag</u>ag<u>ag</u> at

Figure 7A gaggctcgctacaggtattgtaatccgccgttatcgagaagggcagtgtgcccggtagattccggtgaaaataatgtttgaaaataaagtccagtt ctgaaacagagtgccagtattccatgcgaccgcagccagcagcaggtgtaca<u>tata</u>catctcccctccgccgtgatt<u>tgA</u>gcgagaaagaggacatcca <u>ccagccac</u>

Figure 7B

CONTROL OF GENE EXPRESSION IN PLANTS

CROSS-REFERENCE TO RELATED APPLICATIONS

This application is a U.S. National Stage Application under 35 U.S.C. §371 of International Application No. PCT/NZ2010/000056, filed Mar. 26, 2010 and published in English on Oct. 7, 2010 as WO 2010/114395, which claims the benefit of U.S. Provisional Application No. 61/165,776, filed Apr. 1, 2009. Both of these applications are hereby incorporated by reference in their entireties.

TECHNICAL FIELD

The present invention relates to the isolation and use of the polynucleotides for the control of gene expression in plants.

BACKGROUND ART

An important for goal for agriculture is to produce plants with agronomically important traits. Recent advances in genetic manipulation provide the tools to transform plants to contain and express foreign genes. This has led to the development of plants capable of expressing pharmaceuticals and other chemicals, plants with increased pest resistance, increased stress tolerance and many other beneficial traits.

It is often desirable to control expression of a polynucleotide of interest, in a particular tissue, at a particular developmental stage, or under particular conditions, in which the polynucleotide is not normally expressed. The polynucleotide of interest may encode a protein or alternatively may be intended to effect silencing of a corresponding target gene.

Plant promoter sequences are useful in genetic manipulation for directing such spatial, temporal and inducible expression of polynucleotides in transgenic plants. To achieve this, a genetic construct is often introduced into a plant cell or plant. Typically such constructs include a plant promoter operably linked to the polynucleotide sequence of interest. Such a promoter need not normally be associated with the gene of interest. Once transformed, the promoter controls expression of the operably linked polynucleotide of interest thus leading to the desired transgene expression and resulting desired phenotypic characteristics in the plant.

Promoters used in genetic manipulation are typically derived from the 5' un-transcribed region of genes and contain regulatory elements that are necessary to control expression of the operably linked polynucleotide. Promoters useful for plant biotechnology can be classified depending on when and where they direct expression. For example promoters may be tissue specific or constitutive (capable of transcribing sequences in multiple tissues). Other classes of promoters include inducible promoters that can be triggered on external stimuli such as environmental, and chemical stimuli.

It would be beneficial to have a variety of promoters available in order to ensure that transgenes are transcribed efficiently in the right tissues, at an appropriate stage of growth or development. Additionally it may be desirable to direct a gene expression in response to certain environmental or chemicals signals.

Perennial ryegrass (*Lolium perenne* L) is the major grass species grown in New Zealand and other temperate climates throughout the world. Valuable traits that may be improved by genetic manipulation of perennial ryegrass include stress tolerance, disease tolerance and nutritional quality. Genetic manipulation of such traits in perennial ryegrass is limited by the availability of promoters capable of appropriately controlling the expression of genes of interest.

It is therefore an object of the present invention to provide a promoter from ryegrass useful for controlling expression of genes in plants or at least to provide a useful choice.

SUMMARY OF THE INVENTION

In one aspect the invention provides an isolated promoter polynucleotide comprising:
   a) the sequence of SEQ ID NO:1 or 7;
   b) a variant of the sequence of SEQ ID NO:1 or 7;
   c) a fragment of the sequence of SEQ ID NO:1 or 7;
   d) a fragment of the sequence of b);
   e) a variant of the sequence of c); or
   f) the complement any one of a) to e)
wherein the promoter polynucleotide is capable of controlling transcription of an operably linked polynucleotide in a plant.

In one embodiment the isolated promoter polynucleotide comprises:
   a) the sequence of SEQ ID NO:1 or 7;
   b) a sequence with at least 70% identity to the sequence of SEQ ID NO:1 or 7;
   c) at least 50 contiguous nucleotides of the sequence of SEQ ID NO:1 or 7;
   d) at least 50 contiguous nucleotides of the sequence of b);
   e) a sequence with at least 70% identity to the sequence of c); or
   f) the complement of any one of a) to e)
wherein the promoter polynucleotide is capable of controlling transcription of an operably linked polynucleotide in a plant.

In one embodiment the promoter polynucleotide is capable of controlling transcription of an operably linked polynucleotide sequence in at least one of leaves, internodes, roots and flowers.

In a further embodiment the promoter polynucleotide is capable of controlling transcription of an operably linked polynucleotide sequence in leaves.

In a further embodiment the promoter polynucleotide is capable of controlling transcription of an operably linked polynucleotide sequence in internodes.

In a further embodiment the promoter polynucleotide is capable of controlling transcription of an operably linked polynucleotide sequence in roots.

In a further embodiment the promoter polynucleotide is capable of controlling transcription of an operably linked polynucleotide sequence in flowers.

Preferably the promoter polynucleotide is capable of controlling transcription of an operably linked polynucleotide sequence in all of leaves, internodes, roots and flowers.

Preferably the promoter polynucleotide is capable of controlling transcription of an operably linked polynucleotide sequence constitutively in all tissues of a plant.

In a further aspect the invention provides a genetic construct comprising a promoter polynucleotide of the invention.

In one embodiment the promoter polynucleotide is operably linked to a polynucleotide sequence to be expressed.

In a further aspect the invention provides a vector comprising a genetic construct of the invention.

In a further aspect the invention provides a plant cell or plant transformed with the promoter polynucleotide of the invention.

In a further aspect the invention provides a plant cell or plant transformed with a genetic construct of the invention.

In a further aspect the invention provides a method for modifying expression of at least one polynucleotide in a plant cell or plant; the method comprising transformation of the plant cell or plant with a promoter polynucleotide of the invention.

In a further aspect the invention provides a method for modifying expression of at least one polynucleotide in a plant cell or plant, the method comprising transformation of the plant cell or plant with a genetic construct of the invention.

In a further aspect the invention provides a method for producing a plant cell or plant with modified expression of at least one polynucleotide, the method comprising:
  (a) transforming plant cell or plant with a promoter polynucleotide of the invention, and
  (b) the cultivating the transgenic plant cell or plant under conditions conducive for the promoter polynucleotide to drive transcription.

In a further aspect the invention provides a method for producing a plant cell or plant with modified expression of at least one polynucleotide, the method comprising:
  (a) transforming plant cell or plant with a genetic construct of the invention, and
  (b) the cultivating the transgenic plant cell or plant under conditions conducive for the promoter polynucleotide to drive transcription.

In a further aspect the invention provides a method for producing a plant cell or plant with modified expression of at least one gene, the method comprising:
  (a) transforming plant cell or plant with a genetic construct of the invention wherein the genetic construct comprises a promoter polynucleotide of the invention operably linked to a polynucleotide sequence to be expressed, and
  (b) the cultivating the transgenic plant cell or plant under conditions conducive for the promoter polynucleotide to drive transcription of operably linked sequence.

It will be appreciated by those skilled in the art that, the promoter polynucleotide of the invention may be transformed into the plant to control expression of a polynucleotide operably linked to the promoter prior to transformation. Alternatively the promoter polynucleotide may be transformed into the genome of the plant without an operably linked polynucleotide, but the promoter may control expression of an endogenous polynucleotide, adjacent to the insert site, and typically, to the 3' end of the inserted promoter polynucleotide.

In a further aspect of the invention provides a method for producing a plant cell or plant with a modified phenotype, the method including the stable incorporation into the genome of the plant, a promoter polynucleotide of the invention.

In a further aspect of the invention provides a method for producing a plant cell or plant with a modified phenotype, the method including the stable incorporation into the genome of the plant, a genetic construct of the invention.

In a further aspect the invention provides a plant cell or plant produced by a method of the invention.

In a further aspect the invention provides a seed, propagule, progeny or part of a plant, of the invention.

In a preferred embodiment the seed, propagule, progeny or part of a plant, of the invention is transformed with a polynucleotide or a construct of the invention.

The promoter polynucleotide of the invention may be derived from any species and/or may be produced synthetically or recombinantly.

In one embodiment the promoter polynucleotide, is derived from a plant species.

In a further embodiment the promoter polynucleotide, is derived from a gymnosperm plant species.

In a further embodiment the promoter polynucleotide, is derived from an angiosperm plant species.

In a further embodiment the promoter polynucleotide, is derived from a from dicotyledonuous plant species.

In a further embodiment the promoter polynucleotide, is derived from a monocotyledonous plant species.

The polypeptide encoded by the polynucleotide to be expressed in the construct of the invention, may be derived from any species and/or may be produced synthetically or recombinantly.

In one embodiment the polypeptide is derived from a plant species.

In a further embodiment the polypeptide is derived from a gymnosperm plant species.

In a further embodiment the polypeptide is derived from an angiosperm plant species.

In a further embodiment the polypeptide is derived from a from dicotyledonous plant species.

In a further embodiment the polypeptide is derived from a monocotyledonous plant species.

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred dicotyledonous plant genera include: Amygdalus, Anacardium, Anemone, Arachis, Brassica, Cajanus, Cannabis, Carthamus, Carya, Ceiba, Cicer, Claytonia, Coriandrum, Coronilla, Corydalis, Crotalaria, Cyclamen, Dentaria, Dicentra, Dolichos, Eranthis, Glycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Oxalis, Papaver, Phaseolus, Phoenix, Pistacia, Pisum, Prunus, Pueraria, Ribes, Ricinus, Sesamum, Thalictrum, Theobroma, Trifolium, Trigonella, Vicia and Vigna.

Preferred dicotyledonous plant species include: Amygdalus communis, Anacardium occidentale, Anemone americana, Anemone occidentalis, Arachis hypogaea, Arachis hypogea, Brassica napus Rape, Brassica nigra, Brassica campestris, Cajanus cajan, Cajanus indicus, Cannabis sativa, Carthamus tinctorius, Carya illinoinensis, Ceiba pentandra, Cicer arietinum, Claytonia exigua, Claytonia megarhiza, Coriandrum sativum, Coronilla varia, Corydalis flavula, Corydalis sempervirens, Crotalaria juncea, Cyclamen coum, Dentaria laciniata, Dicentra eximia, Dicentra formosa, Dolichos lablab, Eranthis hyemalis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus corniculatus, Lupinus albus, Medicago arborea, Medicago falcate, Medicago hispida, Medicago officinalis, Medicago sativa (alfalfa), Medicago tribuloides, Macadamia integrifolia, Medicago arabica, Melilotus albus, Mucuna pruriens, Olea europaea, Onobrychis viciifolia, Ornithopus sativus, Oxalis tuberosa, Phaseolus aureus, Prunus cerasifera, Prunus cerasus, Phaseolus coccineus, Prunus domestica, Phaseolus lunatus, Prunus maheleb, Phaseolus mungo, Prunus persica, Prunus

*pseudocerasus, Phaseolus vulgaris, Papaver somniferum, Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Thalictrum dioicum, Thalictrum flavum, Thalictrum thalictroides, Theobroma cacao, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Trifolium alexandrinum, Trigonella foenumgraecum, Vicia angustifolia, Vicia atropurpurea, Vicia calcarata, Vicia dasycarpa, Vicia ervilia, Vaccinium oxycoccos, Vicia pannonica, Vigna sesquipedalis, Vigna sinensis, Vicia villosa, Vicia faba, Vicia sative* and *Vigna angularis.*

Preferred monocotyledonous plant genera include: *Agropyron, Allium, Alopecurus, Andropogon, Arrhenatherum, Asparagus, Avena, Bambusa, Bellavalia, Brimeura, Brodiaea, Bulbocodium, Bothrichloa, Bouteloua, Bromus, Calamovilfa, Camassia, Cenchrus, Chionodoxa, Chloris, Colchicum, Crocus, Cymbopogon, Cynodon, Cypripedium, Dactylis, Dichanthium, Digitaria, Elaeis, Eleusine, Eragrostis, Eremurus, Erythronium, Fagopyrum, Festuca, Fritillaria, Galanthus, Helianthus, Hordeum, Hyacinthus, Hyacinthoides, Ipheion, Iris, Leucojum, Liatris, Lolium, Lycoris, Miscanthis, Miscanthus×giganteus, Muscari, Ornithogalum, Oryza, Panicum, Paspalum, Pennisetum, Phalaris, Phleum, Poa, Puschkinia, Saccharum, Secale, Setaria, Sorghastrum, Sorghum, Triticum, Vanilla, X Triticosecale Triticale* and *Zea.*

Preferred monocotyledonous plant species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium fistulosum, Allium sativum, Alopecurus pratensis, Andropogon gerardi, Andropogon gerardii, Andropogon scoparious, Arrhenatherum elatius, Asparagus officinalis, Avena nuda, Avena sativa, Bambusa vulgaris, Bellevalia trifoliate, Brimeura amethystina, Brodiaea californica, Brodiaea coronaria, Brodiaea elegans, Bulbocodium versicolor, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Camassia scilloides, Cenchrus ciliaris, Chionodoxa forbesii, Chloris gayana, Colchicum autumnale, Crocus sativus, Cymbopogon nardus, Cynodon dactylon, Cypripedium acaule, Dactylis glomerata, Dichanthium annulatum, Dichanthium aristatum, Dichanthium sericeum, Digitaria decumbens, Digitaria smutsii, Elaeis guineensis, Elaeis oleifera, Eleusine coracan, Elymus angustus, Elymus junceus, Eragrostis curvula, Eragrostis tef Eremurus robustus, Erythronium elegans, Erythronium helenae, Fagopyrum esculentum, Fagopyrum tataricum, Festuca arundinacea, Festuca ovina, Festuca pratensis, Festuca rubra, Fritillaria cirrhosa, Galanthus nivalis, Helianthus annuus sunflower, Hordeum distichum, Hordeum vulgare, Hyacinthus orientalis, Hyacinthoides hispanica, Hyacinthoides non-scripta, Ipheion sessile, Iris collettii, Iris danfordiae, Iris reticulate, Leucojum aestivum, Liatris cylindracea, Liatris elegans, Lilium longiflorum, Lolium multiflorum, Lolium perenne, Lycoris radiata, Miscanthis sinensis, Miscanthus×giganteus, Muscari armeniacum, Muscari macrocarpum, Narcissus pseudonarcissus, Ornithogalum montanum, Oryza sativa, Panicum italicium, Panicum maximum, Panicum miliaceum, Panicum purpurascens, Panicum virgatum, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa nemoralis, Puschkinia scilloides, Saccharum officinarum, Saccharum robustum, Saccharum sinense, Saccharum spontaneum, Scilla autumnalis, Scilla peruviana, Secale cereale, Setaria italica, Setaria sphacelata, Sorghastrum nutans, Sorghum bicolor, Sorghum dochna, Sorghum halepense, Sorghum sudanense, Trillium grandiflorum, Triticum aestivum, Triticum dicoccum, Triticum durum, Triticum monococcum, Tulipa batalinii, Tulipa clusiana, Tulipa dasystemon, Tulipa gesneriana, Tulipa greigii, Tulipa kaufmanniana, Tulipa sylvestris, Tulipa turkestanica, Vanilla fragrans, X Triticosecale* and *Zea mays.*

Other preferred plants are forage plants from a group comprising but not limited to the following genera: *Lolium, Festuca, Dactylis, Bromus, Trifolium, Medicago, Phleum, Phalaris, Holcus, Lotus, Plantago* and *Cichorium.*

Particularly preferred forage plants are from the genera *Lolium* and *Trifolium*. Particularly preferred species are *Lolium perenne* and *Trifolium repens.*

Particularly preferred monocotyledonous plant species are: *Lolium perenne* and *Oryza sativa.*

A particularly preferred plant species is *Lolium perenne.*

DETAILED DESCRIPTION

The applicants have identified a promoter polynucleotide sequence from perennial ryegrass (*Lolium perenne*) and demonstrated that the promoter regulates transcription of an operably linked polynucleotide in at least one of leaves, internodes, roots and flowers. The invention also provides variants and fragments of the promoter polynucleotide. The invention provides genetic constructs and vectors comprising the promoter polynucleotide sequences, and transgenic plant cells and transgenic plants comprising the promoter polynucleotide sequence, genetic constructs, or vectors of the invention.

The invention also provides methods for modifying expression of genes in plants and modifying phenotype in plants, and methods for producing plants with modified gene expression and modified phenotype. The invention further provides plants produced by the methods of the invention.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is preferably at least 15 nucleotides in length. The fragments of the invention preferably comprises at least 20 nucleotides, more preferably at least 30 nucleotides, more preferably at least 40 nucleotides, more preferably at least 50 nucleotides and most preferably at least 60 contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

The term "fragment" in relation to promoter polynucleotide sequences is intended to include sequences comprising cis-elements and regions of the promoter polynucleotide sequence capable of regulating expression of a polynucleotide sequence to which the fragment is operably linked.

Preferably fragments of promoter polynucleotide sequences of the invention comprise at least 20, more preferably at least 30, more preferably at least 40, more preferably at least 50, more preferably at least 100, more preferably at least 150, more preferably at least 200, more preferably at least 250, more preferably at least 300, more preferably at least 350, and most preferably at least 400 nucleotides of the specified polynucleotide sequence.

Fragments of the promoter preferably comprise at least one copy of TTTGAC (W-box promoter motif). Fragments of the promoter preferably comprise at least one copy of AGCCAC (SORLIP1). Fragments of the promoter preferably comprise at least one copy of the sequence TATA (TATA box).

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence, that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably over the entire length of the specified polynucleotide sequence.

The term "derived from" with respect to polynucleotides of the invention being "derived from" a particular genera or species, means that the polynucleotide has the same sequence as a polynucleotide found naturally in that genera or species. The polynucleotide which is derived from a genera or species may therefore be produced synthetically or recombinantly.

Polypeptides and Fragments

The term "polypeptide", as used herein, encompasses amino acid chains of any length but preferably at least 5 amino acids, including full-length proteins, in which amino acid residues are linked by covalent peptide bonds. The polypeptides may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polypeptides disclosed being derived from a particular genera or species, means that the polypeptide has the same sequence as a polypeptide found naturally in that genera or species. The polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polynucleotides and polypeptides possess biological activities that are the same or similar to those of the inventive polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, more preferably at least 50 nucleotide positions, more preferably at least 100 nucleotide positions, more preferably at least 200 nucleotide positions, more preferably at least 300 nucleotide positions, more preferably at least 400 nucleotide positions and most preferably over the entire length of the specified polynucleotide sequence.

Variant promoter polynucleotides of the invention preferably comprise at least one copy of one and most preferably at least one copy of two of the two light-inducible promoter motifs: AGATAG (GATA promoter motif) and AGCCAC (SORLIP1); in addition to at least one copy of one, more preferably at least one copy of two and most preferably at least one copy of three of the following cis-element sequences: TTTGAC (W-box promoter motif), GGCCATTA ("Up1" motif) and TCCTCCTCCTCCTCC (TCC promoter motif). The variant promoter preferably comprises at least one copy of the sequence TATA (TATA box).

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences —a new tool for comparing protein and nucleotide sequences", FEMS Microbiol Lett. 174:247-250), which is publicly available from NCBI (available on the world wide web at ftp<dot>ncbi<dot>nih<dot>gov/blast/). The default parameters of bl2seq are utilized except that filtering of low complexity parts should be turned off.

The identity of polynucleotide sequences may be examined using the following unix command line parameters:
bl2seq-i nucleotideseq1-j nucleotideseq2-F F-p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which is available on the world wide web at www<dot>hgm<dot>mrc<dot>ac<dot>uk/Software/EMBOSS/. The European Bioinformatics Institute server also provides the facility to perform EMBOSS-needle global alignments between two sequences on line at www<dot>ebi<dot>ac<dot>uk/emboss/align/.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [November 2002]) from NCBI (available on the world wide web at ftp<dot>ncbi<dot>nih<dot>gov/blast/).

The similarity of polynucleotide sequences may be examined using the following unix command line parameters:
bl2seq-i nucleotideseq1-j nucleotideseq2-F F-p tblastx The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. Dec. 6, 1991; 254 (5037):1497-500) Tm values are higher than those for DNA-DNA or DNA-RNA hybrids, and can be calculated using the formula described in Giesen et al., Nucleic Acids Res. Nov. 1, 1998; 26(21):5004-6. Exemplary stringent hybridization conditions for a DNA-PNA hybrid having a length less than 100 bases are 5 to 10° C. below the Tm.

Variant polynucleotides such as those in constructs of the invention encoding stress-protective protein, also encompasses polynucleotides that differ from the specified sequences but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also contemplated. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (available on the world wide web at ftp<dot>ncbi<dot>nih<dot>gov/blast/) via the tblastx algorithm as previously described.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain a promoter polynucleotide such as a promoter polynucleotide of the invention including the necessary elements that permit transcribing the insert polynucleotide molecule, and, optionally, translating the transcript into a polypeptide. The insert polynucleotide molecule may be derived from the host cell, or may be derived from a different cell or organism and/or may be a synthetic or recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter, such as a promoter polynucleotide sequence of the invention, functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" includes to untranslated sequences that are upstream of the translational start site and downstream of the translational stop site. These sequences are also referred to respectively as the 5' UTR and the 3' UTR. These sequences may include elements required for transcription initiation and termination and for regulation of translation efficiency. The term "noncoding" also includes intronic sequences within genomic clones.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to a polynucleotide sequence capable of regulating the expression of a polynucleotide sequence to which the promoter is operably linked. Promoters may comprise cis-initiator elements which specify the transcription initiation site and conserved boxes such as the TATA box, and motifs that are bound by transcription factors.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention, or useful in the methods of the invention, include use of all or portions, of the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0. 5% sodium dodecyl sulfate, 1× Denhardt's solution; washing (three washes of twenty minutes each at 55° C.) in 1.0× SSC, 1% (w/v) sodium dodecyl sulfate, and optionally one wash (for twenty minutes) in 0.5× SSC, 1% (w/v) sodium dodecyl sulfate, at 60° C. An optional further wash (for twenty minutes) can be conducted under conditions of 0.1× SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a polynucleotide. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

The promoter sequences disclosed may be characterized to identify fragments, such as cis-elements and regions, capable of regulating to expression of operably linked sequences, using techniques well-known to those skilled in the art. Such techniques include 5' and/or 3' deletion analysis, linker scanning analysis and various DNA footprinting techniques (Degenhardt et al., 1994 Plant Cell:6(8) 1123-34; *Directed Mutagenesis: A Practical Approach IRL Press* (1991)). Fragments include truncated versions of longer promoter sequences which may terminate (at the 3' end) at or close to the transcriptional start site. Methods for identifying the transcription start site of a promoter are well-known to those skilled in the art (discussed in Hashimoto et al., 2004, Nature Biotechnology 22, 1146-1149).

The techniques described above may be used to identify a fragment that defines essential region of the promoter that is able to confer the desired expression profile. The essential region may function by itself or may be fused to a core promoter to drive expression of an operably linked polynucleotide.

The core promoter can be any one of known core promoters such as the Cauliflower Mosaic Virus 35S or 19S promoter (U.S. Pat. No. 5,352,605), ubiquitin promoter (U.S. Pat. No. 5,510,474) the IN2 core promoter (U.S. Pat. No. 5,364,780) or a Figwort Mosaic Virus promoter (Gruber, et al. "Vectors for Plant Transformation" *Methods in Plant Molecular Biology and Biotechnology*) et al. eds, CRC Press pp.89-119 (1993)).

Promoter fragments can be tested for their utility in driving expression in any particular cell or tissue type, or at any particular developmental stage, or in response to any particular stimulus by techniques well-known to those skilled in the art. Techniques include operably-linking the promoter fragment to a reporter or other polynucleotide and measuring report activity or polynucleotide expressions in plants in response to stress. Such techniques are described in Examples section of this specification.

Methods for Identifying Variants
Physical Methods
Variant polynucleotides may be identified using PCR-based methods (Mullis et al., Eds. 1994 The Polymerase Chain Reaction, Birkhauser).

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.
Computer-based Methods
Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which is available on the world wide web at ftp<dot>ncbi<dot>nih<dot>gov/blast/or from the National Center for Biotechnology Information (NCBI), National Library of Medicine, Building 38A, Room 8N805, Bethesda, MD 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity.

For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, (available on the world wide web at www-igbmc<dot>u-strasbg<dot>fr/BioInfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (available on the world wide web at www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Producing Constructs and Vectors

The genetic constructs of the present invention comprise one or more polynucleotide sequences of the invention and/or polynucleotides encoding polypeptides disclosed, and may be useful for transforming, for example, bacterial, fungal, insect, mammalian or particularly plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide. Plants comprising such cells also form an aspect of the invention.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that can be used to genetically transform the following plant species: Rice (Alam et al., 1999, Plant Cell Rep. 18, 572); maize (U.S. Pat. Nos. 5,177, 010 and 5,981,840); wheat (Ortiz et al., 1996, Plant Cell Rep. 15, 1996, 877); tomato (U.S. Pat. No. 5,159,135); potato (Kumar et al., 1996 Plant J. 9, :821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); perennial ryegrass (Bajaj et al., 2006, Plant Cell Rep. 25, 651); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877). Other species are contemplated and suitable methods and protocols are available in the scientific literature for use by those skilled in the art.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. Strategies may also be designed to increase expression of a polynucleotide/polypeptide in response to an external stimulus, such as an environmental stimuli. Environmental stimuli may include environmental stresses such as mechanical (such as herbivore activity), dehydration, salinity and temperature stresses. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed or to reduce expression of a polynucleotide/polypeptide in response to an external stimuli. Such strategies are known as gene silencing strategies.

Genetic constructs for expression of genes in transgenic plants typically include promoters, such as promoter polynucleotides of the invention, for driving the expression of one or more cloned polynucleotide, terminators and selectable marker sequences to detect presence of the genetic construct in the transformed plant.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide may include an antisense copy of a polynucleotide. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'  (coding strand)

3'CTAGAT 5'  (antisense strand)

3'CUAGAU 5' mRNA

5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA . . . TAGATC-3'

3'-CTAGAT . . . ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a sequence operably-linked to promoter of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

Plants

The term "plant" is intended to include a whole plant or any part of a plant, propagules and progeny of a plant.

The term 'propagule' means any part of a plant that may be used in reproduction or propagation, either sexual or asexual, including seeds and cuttings.

A "transgenic" or transformed" plant refers to a plant which contains new genetic material as a result of genetic manipulation or transformation. The new genetic material may be derived from a plant of the same species as the resulting transgenic or transformed plant or from a different species. A transformed plant includes a plant which is either stably or transiently transformed with new genetic material.

The plants of the invention may be grown and either self-ed or crossed with a different plant strain and the resulting hybrids, with the desired phenotypic characteristics, may be identified. Two or more generations may be grown. Plants resulting from such standard breeding approaches also form an aspect of the present invention.

BRIEF DESCRIPTION OF THE DRAWINGS

FIG. 1 shows the promoter polynucleotide sequence of SEQ ID NO:1, showing the predicted transcription start site (uppercase A).

FIG. 2 shows results of a Tf sitescan/dynamicPlus (available on the world wide web at www<dot>ifti<dot>org) (Ghosh D. 2000, Nucleic Acids Research 28:308-10) analysis of the promoter of SEQ ID NO:1.

FIG. 3 shows the results of Signal Scan (available on the world wide web at www<dot>dna<dot>affrc<dot>go<dot>jp/PLACE/signalscan<dot>html) analysis of the promoter of SEQ ID NO:1.

FIG. 7A shows the sequence of the longer (406 bp) promoter of SEQ ID NO:1. B shows the 210 bp fragment of SEQ ID NO:7. Also shown underlined is the position of promoter motifs: GATA promoter motif (AGATAG); SORLIP1 (AGCCAC); W-box promoter motif (TTGAC); "Up1" motif (GGCCATTA); TCC motif (TCCTCCTCCTCCTCC); and TATA box (TATA). The shaded sequence in A is the sequence present in SEQ ID NO: 1 that is absent in SEQ ID NO: 7 in B.

EXAMPLES

The invention will now be illustrated with reference to the following non-limiting examples.

Example 1

Identification and Characterisation of the Ryegrass Promoter Sequence of the Invention Hypomethylated genomic DNA from Lolium perenne cv. Bronsyn was isolated and sequenced (Orion Genomics, St Louis). A hypomethylated genomic DNA sequence of 406 bp (SEQ ID NO:1) was identified as containing a 5' transcriptional regulatory region based on the sequence homology to a 5' CDS. A set of 4 nested primers were designed (SEQ ID NO:3 Flanking forward primer—GGCTCTAGAAAGTTGTTG; SEQ ID NO:4 Flanking reverse primer—AGATTCCCAAAGCTGCTG; SEQ ID NO:5 Nested forward primer GTACATAGCCTCCAAACA; and SEQ ID NO:6 Nested reverse primer—ATCTCTCTCCTCGCTATC) to enable the applicants to clone the promoter from the targeted Lolium perenne genomic DNA.

The applicants predicted the transcription start site using tools available on the world wide web at www.fruitfly.org/seq tools/promoter.html, the result is shown in FIG. 1.

The applicants used both Tf site scan/dynamicPlus (available on the world wide web at www<dot>ifti<dot>org) (Ghosh D. 2000, NAR, 28:308-10) and Signal Scan (available on the world wide web at www.dna.affrc.go.jp/PLACE/signalscan.html) to identify transcription factor binding sites and cis-acting elements in the sequence of SEQ ID NO:1. The results are shown in FIGS. 2 and 3 respectively.

Of the motifs identified, the following motifs are very likely to have an impact as to the manner in which the promoter functions:

GATA promoter motif (AGATAG)—light activated
SORLIP1 (AGCCAC)—light activated
W-box promoter motif (TTGAC)—biotic stress responsive
"Up1" motif (GGCCATTA)—transcription activator involved in axillary growth
TCC motif (TCCTCCTCCTCCTCC)—transcriptional modulator
TATA box (TATA)

Example 2

Figure 4:
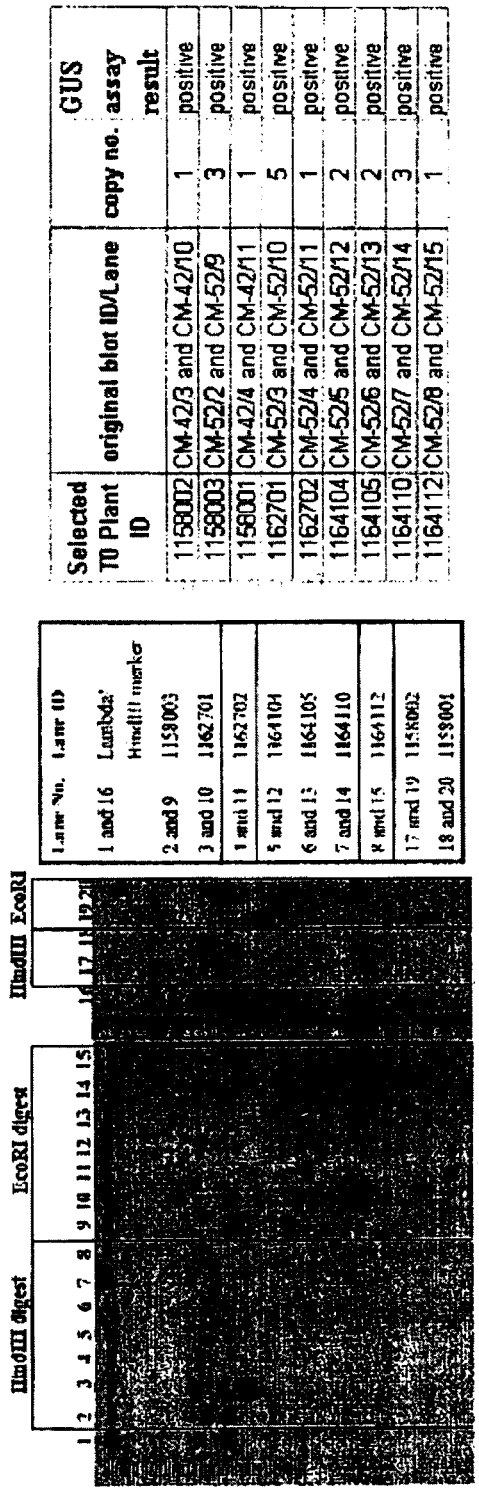
FIG. 4 shows a DNA gel-blot analysis of transgenic ($T_0$) rice lines (1158001, 1158002, 1158003, 1162701, 1162702, 1164104, 1164105, 1164110 and 1164112) transformed with the bacterial uidA gene driven by PRO17.
Figure 5:
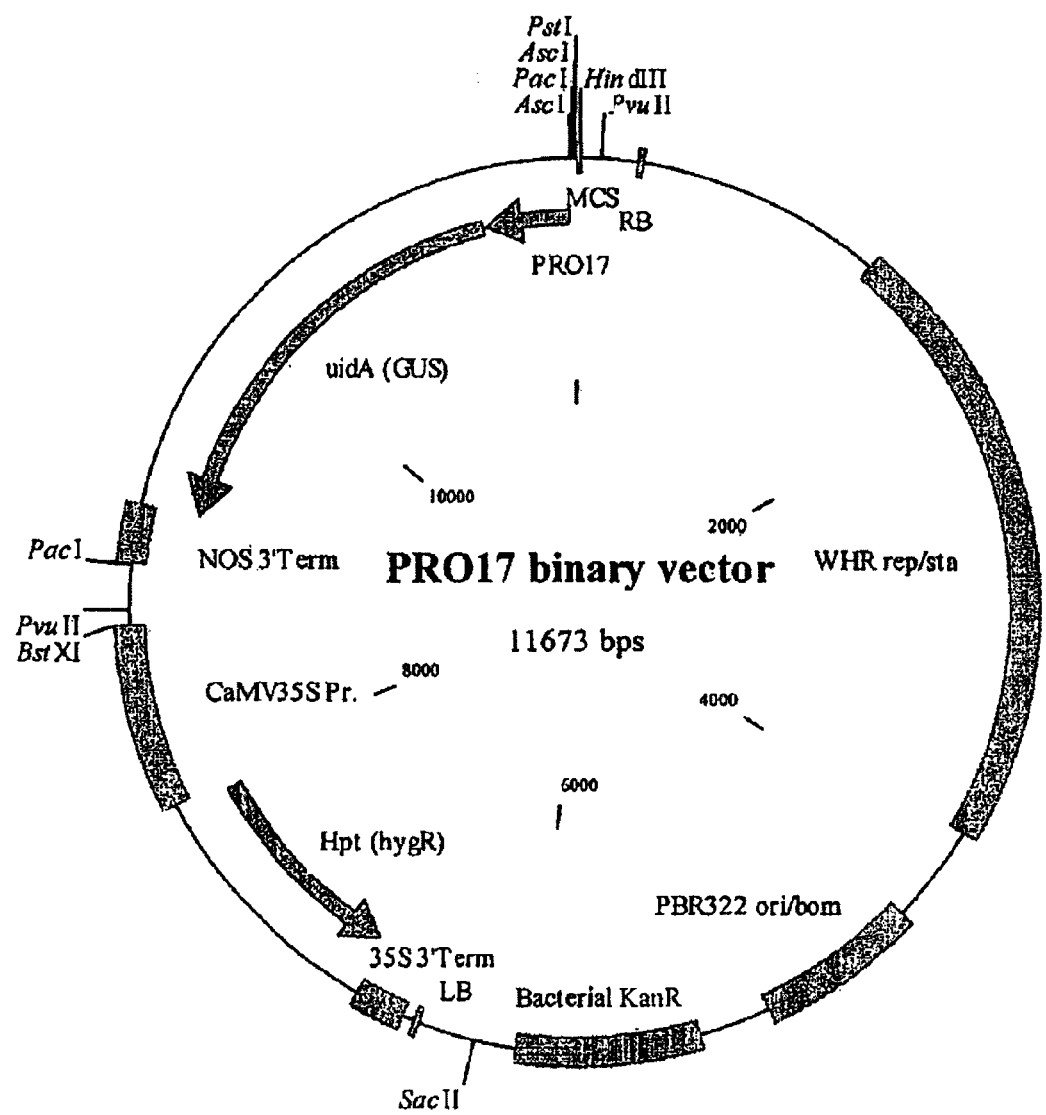
FIG. 5 shows the map of a binary vector including PRO17 operably linked to the bacterial uidA gene.

Demonstration of Control of Gene Expression by the Ryegrass Promoter of the Invention and Fragment Thereof in Plants Preparation of a Promoter Reporter Construct A 406 bp DNA sequence fragment was amplified by PCR from the sequence of SEQ ID NO:1 using two pairs of oligonucleotide sequences (SEQ ID NO: 3 to 6) and inserted into a T-tailed cloning entry vector that enables a transcriptional fusion between the ryegrass promoter and the GUS reporter gene (Jefferson R. A., et al., 1987. EMBO 6:3901-3907). Clones were sequenced and a positive clone was selected based on sequence analysis indicating that the promoter is in the correct orientation to drive the reporter gene. The promoter-reporter and terminator cassette was excised by digesting with the restriction enzyme PacI. The PacI fragment was ligated in the binary vector at the PacI site to result in the PRO17 binary construct. A map of the PRO17 binary construct is shown in FIG. 5. The sequence of the binary construct is shown in SEQ ID NO:2.

Table 1 below shows features of the PRO17 construct.

TABLE 1

Molecule: PRO17, 11673 bps DNA Circular
Description:

| Type | Start | End | C* | Name | Description |
|---|---|---|---|---|---|
| REGION | 261 | 286 | | RB | |
| REGION | 6520 | 6545 | | LB | |
| REGION | 6810 | 6595 | C | 35S 3'Term | |
| GENE | 7861 | 6839 | C | Hpt | |
| Promoter | 8678 | 7897 | C | CaMV35S Pr. | |
| REGION | 9179 | 8937 | C | NOS 3'Term | |
| GENE | 11214 | 9190 | C | uidA | GUS encoding gene with intron |
| Promoter | 11637 | 11230 | C | PRO17 | |

Note:
C* = Complimentary sequence

Preparation of a Promoter Deletion Reporter Construct

Polymerase Chain Reaction (PCR) can be used to make promoter deletions in order to test the control of gene expression by fragments of the promoter. The applicants produced a 210 bp fragment of the promoter of SEQ ID NO:1 by standard PCR techniques. The sequence of the 210 bp fragment is shown in SEQ ID NO:7.

In the 210 bp fragment, the GATA promoter motif, "Up1" motif and TCC motif present in SEQ ID NO:1 are removed. The SORLIP1 motif, W-box promoter motif, TATA box and the trasnscription start site are retained. This is illustrated in FIG. 7, which shows the position of these motifs in the longer promoter of SEQ ID NO:1, and the 210 bp fragment of SEQ ID NO:7

Figure 8:
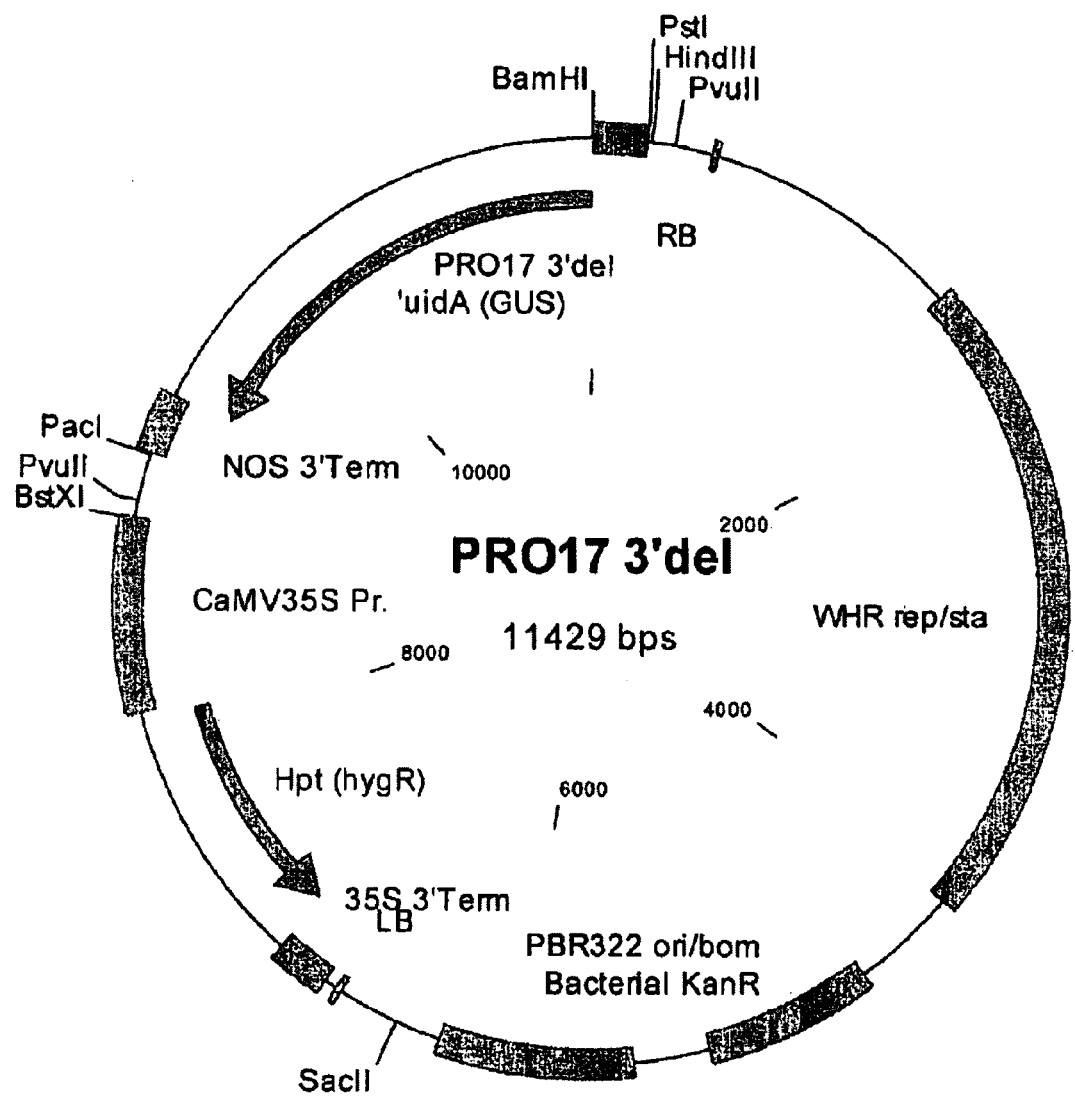
FIG. 8 shows a map of the PRO17 3'deletion construct.

A promoter deletion construct (PRO17 3'deletion construct) with the 210 bp promoter fragment of SEQ ID NO:7 driving expression of the GUS gene was produced by standard techniques. A map of the PRO17 3'deletion construct is shown in FIG. 8. Table 2 below shows features of the PRO17 3'deletion construct.

TABLE 2

Molecule: PRO17 3'del, 11429 bps DNA Circular

| Start | End | | Name |
|---|---|---|---|
| 218 | 9 | C* | PRO17 3'del |
| 483 | 508 | | RB |
| 1549 | 4132 | | WHR rep/sta |
| 4552 | 5232 | | PBR322 ori/bom |
| 5535 | 6317 | | Bacterial KanR |
| 6742 | 6767 | | LB |
| 7032 | 6817 | C | 35S 3'Term |
| 8083 | 7061 | C | Hpt (hygR) |
| 8900 | 8119 | C | CaMV35S Pr. |
| 9401 | 9159 | C | NOS 3'Term |
| 11427 | 9412 | C | uidA (GUS)GUS encoding gene with intron |

Note:
*C = Complimentary sequence

The sequence of the PRO17 3'deletion construct is shown in SEQ ID NO:8.

Control Double 35S Promoter: GUS Construct

Figure 10:
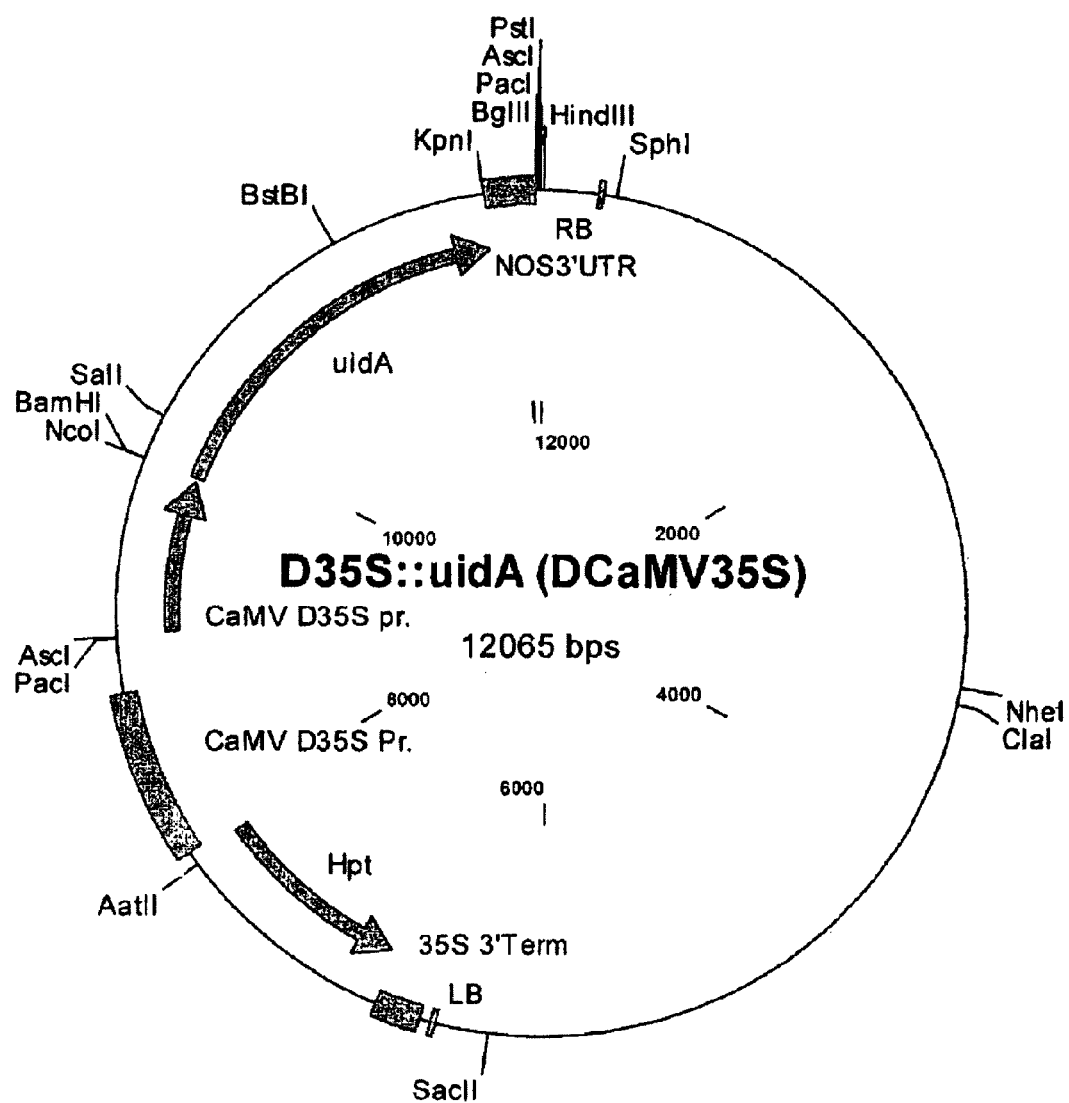
FIG. 10 shows a map of the binary vector D35S::uidA (DCaMV35S) including CaMV D35S promoter operably linked to the bacterial uidA gene.

A control construct with a double CaMV35 promoter driving expression of the GUS reporter gene was also prepared by standard techniques. The sequence of the double CaMV35S promoter used is shown in SEQ ID NO: 21. The sequence of the whole construct is shown in SEQ ID NO: 22. A map of the control construct is shown in FIG. 10. Table 3 below shows features of the control construct (D35S::uidA [DCAMV35S]).

TABLE 3

Molecule: D35S::uidA (DCaMV35S), 12065 bps DNA Circular

| Start | End | | Name |
|---|---|---|---|
| 261 | 286 | | RB |
| 6520 | 6545 | | LB |
| 6810 | 6595 | C* | 35S 3'Term |
| 7861 | 6839 | C* | Hpt |
| 8678 | 7894 | C* | CaMV D35S Pr. |
| 8953 | 9749 | | CaMV D35S pr. |
| 9767 | 11792 | | uidA |
| 11802 | 12038 | | NOS3'UTR |

Note:
C* = Complimentary sequence

Transformation of Plants with the Promoter Constucts

Rice Transformation

Figure 6:
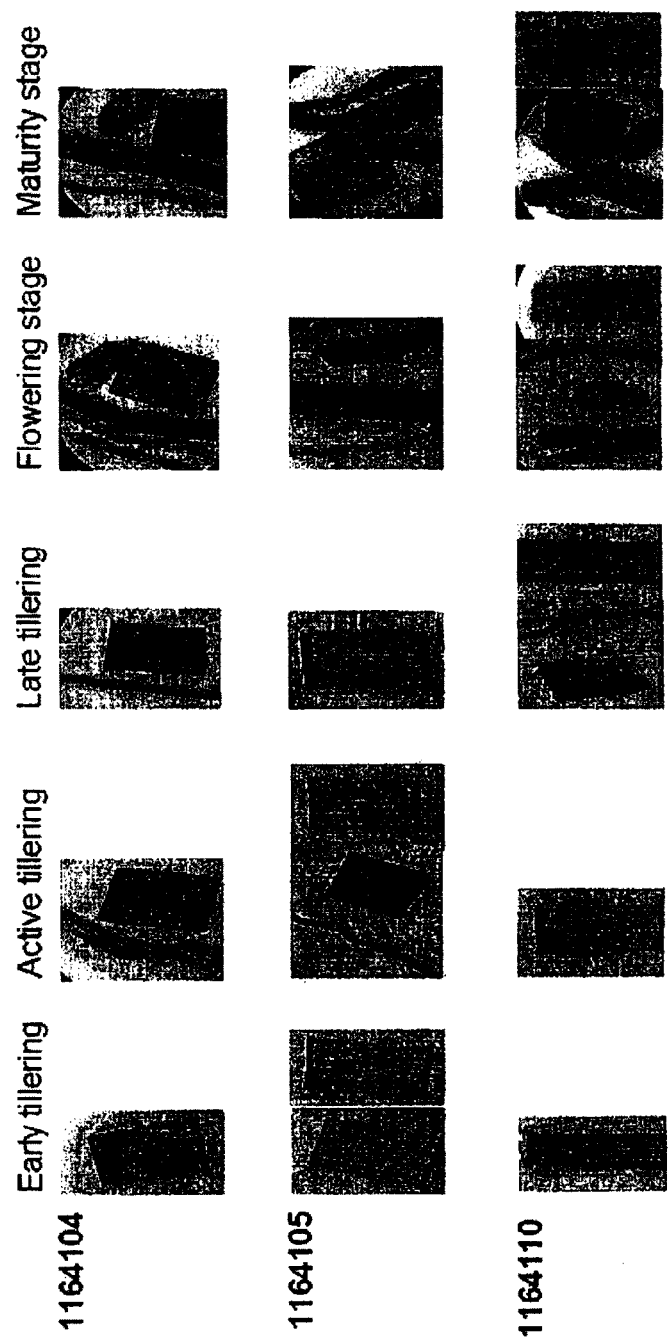
FIG. 6 shows the results from histochemical examination for bacterial uidA expression by GUS activity analysis in three independent transgenic lines (1164104, 1164105 and 1164110) of rice.

Rice (*Oryza sativa* spp *japonica* cv. Niponbarre) was transformed using an immature embryo based system (Metahelix Life Sciences, India). Immature panicles, post-milky stage were used to source embryos. Freshly isolated immature embryos were co-cultivated with *Agrobacterium tumefaciens* (*A. tumefaciens*) harboring the promoter/GUS binary construct (PRO17) described above for 48-64 h. *A. tumefaciens* were eliminated by antibiotic treatment and the explants were transferred to selection medium where the transformed plant cells proliferate to give rise to uniformly transformed calli. The selection medium had a combination of 2,4-D and benzylaminopurine. After 3-4 weeks of selection, the calli were transferred to a regeneration medium containing increased cytokinin and decreased auxin concentration relative to the selection medium. Shoot and root were initiated in this medium. Plantlets were transferred to a glasshouse for hardening. Forty three primary transformed ($T_0$) plants from eighteen different independent transformation events were established in the glasshouse. Twenty seeds each from three of the six $T_0$ events were grown to produce $T_1$ plants, which were pheotyped for GUS expression and activity (Tables 4 and 5; FIG. 6).

Ryegrass Transformation

Perennial ryegrass (*Lolium perenne* L. cv. *Tolosa*) was separately transformed with the PRO17, PRO17 3' deletion and double 35S:GUS constructs described above, essentially as described in Bajaj et. al. (Plant Cell Reports 2006 25: 651-659). Embryogenic callus derived from mersitematic regions of the tillers of selected ryegrass lines and *Agrobacterium tumefaciens* strain EHA101 carrying the appropriate vector were used for transformation experiments. Embryogenic calli were immersed with overnight-grown *Agrobacterium* cultures for 30 minutes with continuous shaking. Calli resistant to hygromycin were selected after subculturing them on co-cultivation medium for 4 weeks. After selection, the resistant calli were subcultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup. We generated and analysed seven independent transgenic events for PRO17, six independent transgenic events for PRO17 3' deletion and two independent transgenic events for 35S:GUS constructs.

Tissue Specificity of the Promoter

Rice tissue samples from various tissues and developmental stages were stained in GUS staining solution (Jefferson R. A., et al., 1987. EMBO 6:3901-3907). The results (Table 4 and 5; and FIG. 6) show that this ryegrass gene promoter has a moderate level of expression in all tissues of rice (leaf, root, spikelet and internodes) and throughout the rice's growth stages

TABLE 4

| | Qualitative GUS assay | | | | | |
| | PRO17 | | | DCaMV35S | | |
| Different stages of Histochemical GUS staining | 1164104 Staining result | 1164105 Staining result | 1164110 Staining result | 1093001 Staining result | 1093004 Staining result | Wild Type Staining result |
|---|---|---|---|---|---|---|
| Early tillering stage | | | | | | |
| Leaf | Positive | Positive | Positive | Positive | Positive | Negative |
| Active tillering stage | | | | | | |
| Leaf | Positive | Positive | Positive | Positive | Positive | Negative |
| Root | Positive | Positive | Positive | Positive | Positive | Negative |
| Late tillering stage | | | | | | |
| Leaf | Positive | Positive | Positive | Positive | Positive | Negative |
| Flowering stage | | | | | | |
| Leaf | Positive | Positive | Positive | Positive | Positive | Negative |
| Internode | Positive | Positive | Positive | Positive | Positive | Negative |
| Root | Positive | mild staining | Positive | Positive | Positive | Negative |
| Spikelet | Positive | Positive | Positive | Positive | Positive | Negative |
| Maturity stage | | | | | | |
| Leaf | Positive | Positive | Positive | Positive | Positive | Negative |
| Internode | Positive | Positive | Positive | Positive | Positive | Negative |
| Root | Positive | mild staining | Positive | Positive | Positive | Negative |
| Spikelet | Positive | mild staining | Positive | Positive | Positive | Negative |

TABLE 5

| construct ID | Event ID | Activity of the extract (pmol/min/μg) |
|---|---|---|
| PRO17 | 1164104 | 12.64 |
| PRO17 | 1164105 | 7.99 |
| PRO17 | 1164110 | 18.54 |
| D35sP | 1093001 | 0.08 |
| D35sP | 1093004 | 53.73 |
| control | Nipponbare | 0.07 |

Comparison of Activity of Full Length Promoter and Fragment Thereof

The activity of the PRO17 deletion promoter was compared to that of the full-length PRO17 promoter and the double 35S GUS promoter (as described in above) in respective transgenic plants, by real time PCR analysis as follows.

RNA Extraction and mRNA Isolation

Frozen ryegrass leaf tissues harvested from plants growing in tissue culture vessels were ground independently in liquid nitrogen. Total RNA was extracted using the RNeasy Plant Mini Kit (Qiagen, Hilden, Germany) according to the manufacturers' protocol. Residual genomic DNA was removed by on-column DNAse I digestion, using the RNase-free DNase set (Qiagen), and mRNA was purified from total RNA using Dynabeads® Oligo (dT)25 (Invitrogen Dynal AS, Oslo, Norway). The mRNA concentration and purity were determined using a Nanodrop ND-1000 spectrophotometer (Nanodrop Technologies, Wilmington, Del., USA); each mRNA sample was assayed twice and an average value determined.

First Strand cDNA Synthesis

Messenger RNA (10 ng) was reverse transcribed to produce cDNA using the Transcriptor cDNA Synthesis Kit (Roche Applied Science, Mannheim, Germany) with anchored-oligo (dT)18 primers in total reaction volumes of 20 μl. All cDNA samples were diluted ten-fold with PCR-grade water before, further use.

Real-Time qRT-PCR Conditions and Analysis

The real-time qRT-PCR were performed in 384-well plates with a LightCycler® 480 real-time PCR instrument (Roche Diagnostics, Mannheim, Germany), using the LightCycler® 480 SYBR Green I Master kit. The reaction set-up was performed on the epMotion® 5075LH automated liquid handling system (Eppendorf, Hamburg, Germany). Reactions contained 5 μl SYBR Green I Master, 2 μl PCR-grade water, 2 μl cDNA and 0.5 μl of each of the 10 μM forward and reverse gene-specific primers in a final volume of 10 μl. Each PCR reaction was performed in triplicate and no-template controls added. The reactions were incubated at 95° C. for 5 min to activate the FastStart Taq DNA polymerase, followed by 55 cycles of 95° C. for 10 sec, 55° C. for 10 sec, and 72° C. for 8 sec. The specificity of the PCR reaction was checked with a heat dissociation protocol (from 60° C. to 95° C.) following the final PCR cycle. This ensured that the resulting fluorescence originated from a single PCR product and did not represent primer-dimers formed during PCR or a non-specific product. Samples were analysed using the Abs Quant/2nd Derivative Max analysis contained in the LightCycler® 480 software. This analysis calculates the Cp value for each PCR reaction; a smaller value is indicative of abundant transcript while larger value indicates rare transcripts. The Cp values were imported into Microsoft Excel Spreadsheet and data from all transgenic plants were normalised against the average of three reference genes (eEF1A, YT521-B and eIF4A) (Lee J M, Roche J R, Donaghy D J, Thrush A and Sathish P. (2010): Validation of reference genes for quantitative RT-PCR studies of gene expression in perennial ryegrass (Lolium perenne L.) BMC Molecular Biology 11:8) before comparing the relative abundance of a native Chlorophyll a/b binding protein gene transcript, transgenic hptII transcript driven by CaMV D35S promoter and transgenic uidA transcripts produced by different promoters; CaMV D35S (control) promoter, PRO17 and PRO17 3'deletion. Deleting the 3' end of the PRO17 decreased the promoter activity as is seen by the uidA transcript levels in PRO17 deletion::uidA transformation events.

The following primers were used:

| SEQ ID NO: | Reference | Sequence |
|---|---|---|
| 9 | eEF1A Forward primer | CCGTTTTGTCGAGTTTGGT |
| 10 | eEF1A Reverse primer | AGCAACTGTAACCGAACATAGC |
| 11 | YT521-B Forward primer | TGTAGCTTGATCGCATACCC |
| 12 | YT521-B Reverse primer | ACTCCCTGGTAGCCACCTT |
| 13 | eIF4A Forward primer | AACTCAACTTGAAGTGTTGGAGTG |
| 14 | eIF4A Reverse primer | AGATCTGGTCCTGGAAAGAATATG |
| 15 | CAB Forward primer | GTCTCGACTACCTCGGCAAC |
| 16 | CAB Reverse primer | ACCGAACATGGAGAACATGG |
| 17 | uidA Forward primer | GAAACTGCATCAGCCGATTA |
| 18 | uidA Reverse primer | TTCACCGAAGTTCATGCCAG |
| 19 | hptII Forward primer | AATACGAGGTCGCCAACATCT |
| 20 | hptII Reverse primer | AGGAACCCTAATTCCCTTATCTG |

Figure 9:
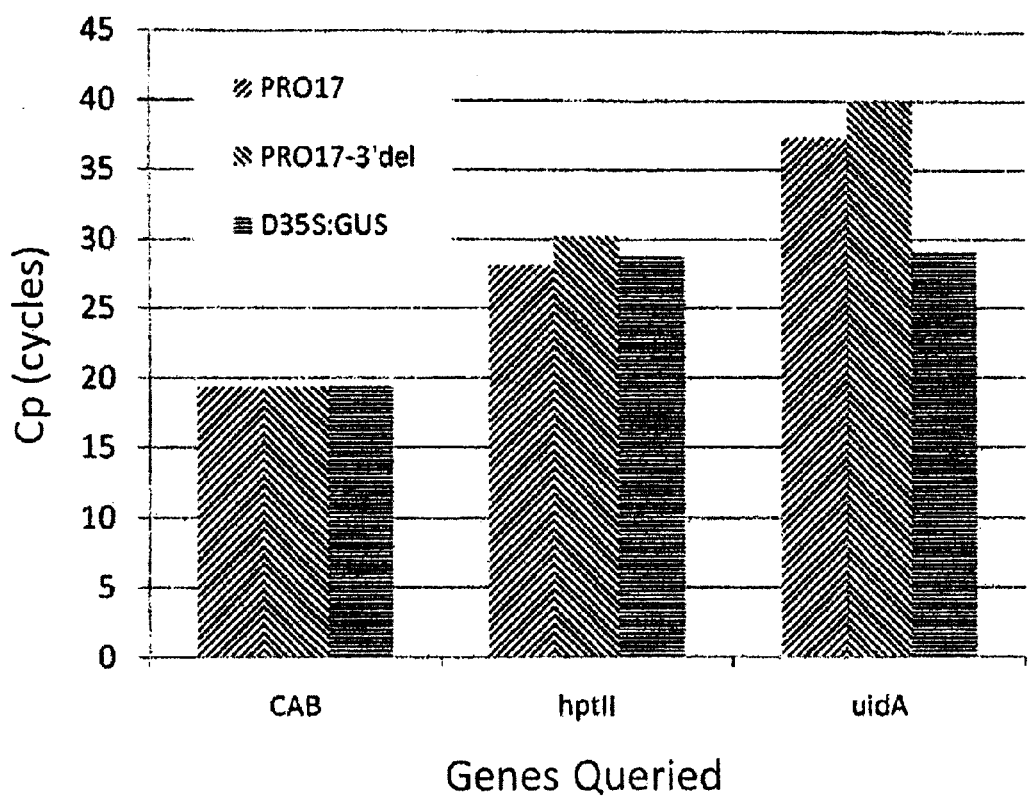
FIG. 9 shows qRT-PCR analysis of gene expression using 0.1 ng of mRNA from $T_0$ perennial ryegrass plants transformed with different promoter-reporter (uidA) constructs. Data is normalized to constant expression of the native chlorophyll a/b binding protein gene expression across all transformation events after normalising the data in each line using the three reference genes (eEF1A, YT521-B and eIF4A). Data is the average of gene expression levels monitored in two D35S::uidA & D35S::hptII events; seven PRO17::uidA & D35S::hptII events; and six PRO17 3' del::uidA & D35S::hptII events.

FIG. 9 shows qRT-PCR analysis of gene expression using 0.1 ng of mRNA from $T_0$ perennial ryegrass plants transformed with different promoter-reporter (uidA) constructs. Data is normalized to constant expression of the native chlorophyll a/b binding protein gene expression across all transformation events after normalising the data in each line using the three reference genes (eEF1A, YT521-B and eIF4A). Data is the average of gene expression levels monitored in two D35S::uidA & D35S::hptII events; seven PRO17::uidA & D35S::hptII events; and six PRO17 3' del::uidA & D35S::hptII events.

The results show that the shorter 210 bp fragment (SEQ ID NO: 7) of the promoter is also capable of driving expression of an operably linked polynucleotide in plants, albeit at a slightly lower level than that shown by the 406 bp promoter (SEQ ID NO: 1).

The above Examples illustrate practice of the invention. It will be appreciated by those skilled in the art that numerous variations and modifications may be made without departing from the spirit and scope of the invention.

Summary of Sequence Listing

| SEQ ID NO | Type | Species/Artificial | Description |
|---|---|---|---|
| 1 | Polynucleotide | Lolium perenne | PRO17 promoter 406 bp |
| 2 | Polynucleotide | Artificial, construct | PRO17 binary construct |
| 3 | Polynucleotide | Artificial, primer | Flanking forward primer |
| 4 | Polynucleotide | Artificial, primer | Flanking reverse primer |
| 5 | Polynucleotide | Artificial, primer | Nested forward primer |
| 6 | Polynucleotide | Artificial, primer | Nested reverse primer |
| 7 | Polynucleotide | Lolium perenne | PRO17 promoter 210 bp fragment |
| 8 | Polynucleotide | Artificial, construct | PRO17 3'deletion construct |
| 9 | Polynucleotide | Artificial, primer | eEF1A Forward primer |
| 10 | Polynucleotide | Artificial, primer | eEF1A Reverse primer |
| 11 | Polynucleotide | Artificial, primer | YT521-B Forward primer |
| 12 | Polynucleotide | Artificial, primer | YT521-B Reverse primer |
| 13 | Polynucleotide | Artificial, primer | eIF4A Forward primer |
| 14 | Polynucleotide | Artificial, primer | eIF4A Reverse primer |
| 15 | Polynucleotide | Artificial, primer | CAB Forward primer |
| 16 | Polynucleotide | Artificial, primer | CAB Reverse primer |
| 17 | Polynucleotide | Artificial, primer | uidA Forward primer |
| 18 | Polynucleotide | Artificial, primer | uidA Reverse primer |
| 19 | Polynucleotide | Artificial, primer | hptII Forward primer |
| 20 | Polynucleotide | Artificial, primer | hptII Reverse primer |
| 21 | Polynucleotide | Artificial | double CaMV35S promoter |
| 22 | Polynucleotide | Artificial, construct | double CaMV35S:GUS vector |

The invention claimed is:

1. A plant cell or plant comprising a promoter polynucleotide comprising at least one of:
 a) the sequence of SEQ ID NO:1 or 7; and
 b) a sequence with at least 95% sequence identity to the sequence of SEQ ID NO:1 or 7;
wherein the promoter polynucleotide controls transcription of an operably linked polynucleotide in a plant, wherein the promoter polynucleotide is not normally associated with the operably linked polynucleotide, and wherein the plant cell or plant comprises the promoter polynucleotide as a result of the plant cell or plant, or an ancestor of the plant cell or plant, being transformed with the promoter polynucleotide.

2. The plant cell or plant of claim 1, wherein the promoter polynucleotide is part of a genetic construct.

3. The plant cell or plant of claim 2, wherein the construct comprises the promoter polynucleotide operably linked to a polynucleotide sequence to be expressed.

4. A method for modifying expression of at least one polynucleotide in a plant cell or plant, the method comprising transforming the plant cell or plant with the promoter polynucleotide comprising at least one of:

a) the sequence of SEQ ID NO:1 or 7; and
b) a sequence with at least 95% sequence identity to the sequence of SEQ ID NO:1 or 7.

5. The method of claim 4 wherein the promoter polynucleotide is part of a genetic construct.

6. A method for producing a plant cell or plant with modified expression of at least one polynucleotide, the method comprising:
   (a) transforming the plant cell or plant with a promoter comprising at least one of:
      i) the sequence of SEQ ID NO:1 or 7; and
      ii) a sequence with at least 95% sequence identity to the sequence of SEQ ID NO:1 or 7, and
   (b) cultivating the transgenic plant cell or plant under conditions conducive for the promoter polynucleotide to drive transcription.

7. The method of claim 6 wherein the polynucleotide is part of a genetic construct.

8. A method for producing a plant cell or plant with a modified phenotype, the method including the stable incorporation of a promoter polynucleotide comprising at least one of:
   i) the sequence of SEQ ID NO:1 or 7; and
   ii) a sequence with at least 95% sequence identity to the sequence of SEQ ID NO:1 or 7 into the genome of the plant cell or plant by genetic transformation.

9. The method of claim 8 wherein the promoter polynucleotide is part of a genetic construct.

10. A plant cell or plant of claim 1, that has modified expression of the operably linked polynucleotide.

11. A seed, propagule, progeny or part of a plant of claim 1, wherein the seed, propagule, progeny or part of the plant, or an ancestor of the seed, propagule, progeny or part, comprises the promoter polynucleotide.

12. The seed, propagule, progeny or part of a plant of claim 11, wherein the promoter polynucleotide is part of a genetic construct.

* * * * *

SEQUENCE LISTING

```
<160> NUMBER OF SEQ ID NOS: 22

<210> SEQ ID NO 1
<211> LENGTH: 406
<212> TYPE: DNA
<213> ORGANISM: Lolium perenne

<400> SEQUENCE: 1
gtacatagcc tccaaacatt cttagaggct cgctacaggt attgtaatcc gccgttatcg      60 gagaagggc agtgtgcccg gtagatttcc ggtgaaaata atgtttggaa aaataaagtc     120
cagttctgaa acagagtgcc agtattccat gcgaccgcag cagccagcag gtgtacatat     180
acatctcccc ctccgccgtg atttgacgcg agaaagagga catccaccag ccacactcac     240
acaaacagcc ccggctagtt cccccacctt tcccttcct tccactccgc atccatctcc     300
catctccggc ccattaatat ccaccacctc ctcctcctcc tcctcctcct cctccaagtc     360
gccattactg ccgtagacgg agctgcgaga tagcgaggag agagat                    406

<210> SEQ ID NO 2
<211> LENGTH: 11673
```

```
<212> TYPE: DNA
<213> ORGANISM: Artificial Sequence
<220> FEATURE:
<223> OTHER INFORMATION: Synthetic vector

<400> SEQUENCE: 2
ggaattcgat atcaagcttg gcactggccg tcgttttaca acgtcgtgac tgggaaaacc      60
ctggcgttac ccaacttaat cgccttgcag cacatccccc tttcgccagc tggcgtaata    120
gcgaagaggc ccgcaccgat cgcccttccc aacagttgcg cagcctgaat ggcgaatgct    180
agagcagctt gagcttggat cagattgtcg tttcccgcct tcagtttaaa ctatcagtgt    240
ttgacaggat atattggcgg gtaaacctaa gagaaaagag cgtttattag aataacggat    300
atttaaaagg cgtgaaaag gtttatccgt tcgtccattt gtatgtgcat gccaaccaca    360
gggttcccct cgggatcaaa gtactttgat ccaacccctc cgctgctata gtgcagtcgg    420
cttctgacgt tcagtgcagc cgtcttctga aaacgacatg tcgcacaagt cctaagttac    480
gcgacaggct gccgccctgc ccttttcctg gcgttttctt gtcgcgtgtt ttagtcgcat    540
aaagtagaat acttgcgact agaaccggag acattacgcc atgaacaaga gcgccgccgc    600
tggcctgctg ggctatgccc gcgtcagcac cgacgaccag gacttgacca accaacgggc    660
cgaactgcac gcggccggct gcaccaagct gttttccgag aagatcaccg gcaccaggcg    720
cgaccgcccg gagctggcca ggatgcttga ccacctacgc cctggcgacg ttgtgacagt    780
gaccaggcta gaccgcctgg cccgcagcac ccgcgaccta ctggacattg ccgagcgcat    840
ccaggaggcc ggcgcgggcc tgcgtagcct ggcagagccg tgggccgaca ccaccacgcc    900
ggccggccgc atggtgttga ccgtgttcgc cggcattgcc gagttcgagc gttccctaat    960
catcgaccgc acccggagcg ggcgcgaggc cgccaaggcc cgaggcgtga agtttggccc   1020
ccgccctacc ctcaccccgg cacagatcgc gcacgcccgc gagctgatcg accaggaagg   1080
ccgcaccgtg aaagaggcgg ctgcactgct tggcgtgcat cgctcgaccc tgtaccgcgc   1140
acttgagcgc agcgaggaag tgacgcccac cgaggccagg cggcgcggtg ccttccgtga   1200
ggacgcattg accgaggccg acgccctggc ggccgccgag aatgaacgcc aagaggaaca   1260
agcatgaaac cgcaccagga cggccaggac gaaccgtttt tcattaccga agagatcgag   1320
gcggagatga tcgcggccgg gtacgtgttc gagccgcccg cgcacgtctc aaccgtgcgg   1380
ctgcatgaaa tcctggccgg tttgtctgat gccaagctgg cggcctggcc ggccagcttg   1440
gccgctgaag aaaccgagcg ccgccgtcta aaaggtgat gtgtatttga gtaaaacagc   1500
ttgcgtcatg cggtcgctgc gtatatgatg cgatgagtaa ataaacaaat acgcaagggg   1560
aacgcatgaa ggttatcgct gtacttaacc agaaaggcgg gtcaggcaag acgaccatcg   1620
caacccatct agcccgcgcc ctgcaactcg ccggggccga tgttctgtta gtcgattccg   1680
atccccaggg cagtgcccgc gattgggcgg ccgtgcggga agatcaaccg ctaaccgttg   1740
tcggcatcga ccgcccgacg attgaccgcg acgtgaaggc catcggccgg cgcgacttcg   1800
tagtgatcga cggagcgccc caggcggcgg acttggctgt gtccgcgatc aaggcagccg   1860
acttcgtgct gattccggtg cagccaagcc cttacgacat atgggccacc gccgacctgg   1920
tggagctggt taagcagcgc attgaggtca cggatgaag ctacaagcg cctttgtcg   1980
tgtcgcgggc gatcaaaggc acgcgcatcg gcggtgaggt tgccgaggcg ctggccgggt   2040
acgagctgcc cattcttgag tcccgtatca cgcagcgcgt gagctaccca ggcactgccg   2100
ccgccggcac aaccgttctt gaatcagaac ccgagggcga cgctgcccgc gaggtccagg   2160
```

```
cgctggccgc tgaaattaaa tcaaaactca tttgagttaa tgaggtaaag agaaaatgag    2220
caaaagcaca aacacgctaa gtgccggccg tccgagcgca cgcagcagca aggctgcaac    2280
gttggccagc ctggcagaca cgccagccat gaagcgggtc aactttcagt tgccggcgga    2340
ggatcacacc aagctgaaga tgtacgcggt acgccaaggc aagaccatta ccgagctgct    2400
atctgaatac atcgcgcagc taccagagta aatgagcaaa tgaataaatg agtagatgaa    2460
ttttagcggc taaaggaggc ggcatggaaa atcaagaaca accaggcacc gacgccgtgg    2520
aatgccccat gtgtggagga acgggcggtt ggccaggcgt aagcggctgg gttgtctgcc    2580
ggccctgcaa tggcactgga accccaagcc ccgaggaatc ggcgtgacgg tcgcaaacca    2640
tccggcccgg tacaaatcgg cgcggcgctg ggtgatgacc tggtggagaa gttgaaggcc    2700
gcgcaggccg cccagcggca acgcatcgag gcagaagcac gccccggtga atcgtggcaa    2760
gcggccgctg atcgaatccg caaagaatcc cggcaaccgc cggcagccgg tgcgccgtcg    2820
attaggaagc cgcccaaggg cgacgagcaa ccagattttt tcgttccgat gctctatgac    2880
gtgggcaccc gcgatagtcg cagcatcatg gacgtggccg ttttccgtct gtcgaagcgt    2940
gaccgacgag ctggcgaggt gatccgctac gagcttccag acgggcacgt agaggtttcc    3000
gcagggccgg ccgcatggc cagtgtgtgg gattacgacc tggtactgat ggcggtttcc    3060
catctaaccg aatccatgaa ccgataccgg gaagggaagg agacaagcc cggccgcgtg    3120 ttccgtccac acgttgcgga cgtactcaag ttctgccggc gagccgatgg cggaaagcag    3180
aaagacgacc tggtagaaac ctgcattcgg ttaaacacca cgcacgttgc catgcagcgt    3240
acgaagaagg ccaagaacgg ccgcctggtg acggtatccg agggtgaagc cttgattagc    3300
cgctacaaga tcgtaaagag cgaaaccggg cggccggagt acatcgagat cgagctagct    3360
gattggatgt accgcgagat cacagaaggc aagaacccgg acgtgctgac ggttcacccc    3420
gattactttt tgatcgatcc cggcatcggc cgttttctct accgcctggc acgccgcgcc    3480
gcaggcaagg cagaagccag atggttgttc aagacgatct acgaacgcag tggcagcgcc    3540
ggagagttca agaagttctg tttcaccgtg cgcaagctga tcgggtcaaa tgacctgccg    3600
gagtacgatt tgaaggagga ggcggggcag gctggcccga tcctagtcat gcgctaccgc    3660
aacctgatcg agggcgaagc atccgccggt tcctaatgta cggagcagat gctagggcaa    3720
attgccctag caggggaaaa aggtcgaaaa ggtctctttc ctgtggatag cacgtacatt    3780
gggaacccaa agccgtacat tgggaaccgg aacccgtaca ttgggaaccc aaagccgtac    3840
attgggaacc ggtcacacat gtaagtgact gatataaaag agaaaaaagg cgattttcc     3900 gcctaaaact cttaaaact tattaaaact cttaaaaccc gcctggcctg tgcataactg    3960
tctggccagc gcacagccga agagctgcaa aaagcgccta cccttcggtc gctgcgctcc    4020
ctacgccccg ccgcttcgcg tcggcctatc gcggccgctg gccgctcaaa atggctggc     4080 ctacggccag gcaatctacc agggcgcgga caagccgcgc cgtcgccact cgaccgccgg    4140
cgcccacatc aaggcaccct gcctcgcgcg tttcggtgat gacggtgaaa acctctgaca    4200
catgcagctc ccggagacgg tcacagcttg tctgtaagcg gatgccggga gcagacaagc    4260
ccgtcagggc gcgtcagcgg gtgttggcgg gtgtcgggc gcagccatga cccagtcacg    4320
tagcgatagc ggagtgtata ctggcttaac tatgcggcat cagagcagat tgtactgaga    4380
gtgcaccata tgcggtgtga atacccgcac agatgcgtaa ggagaaaata ccgcatcagg    4440
cgctcttccg cttcctcgct cactgactcg ctgcgctcgg tcgttcggct gcggcgagcg    4500
gtatcagctc actcaaaggc ggtaatacgg ttatccacag aatcagggga taacgcagga    4560
```

```
aagaacatgt gagcaaaagg ccagcaaaag gccaggaacc gtaaaaaggc cgcgttgctg    4620 gcgttttttcc ataggctccg ccccctgac gagcatcaca aaaatcgacg ctcaagtcag    4680
aggtggcgaa acccgacagg actataaaga taccaggcgt ttccccctgg aagctccctc    4740
gtgcgctctc ctgttccgac cctgccgctt accggatacc tgtccgcctt tctcccttcg    4800
ggaagcgtgg cgctttctca tagctcacgc tgtaggtatc tcagttcggt gtaggtcgtt    4860
cgctccaagc tgggctgtgt gcacgaaccc cccgttcagc ccgaccgctg cgccttatcc    4920
ggtaactatc gtcttgagtc caacccgta agacacgact tatcgccact ggcagcagcc    4980
actggtaaca ggattagcag agcgaggtat gtaggcggtg ctacagagtt cttgaagtgg    5040
tggcctaact acggctacac tagaaggaca gtatttggta tctgcgctct gctgaagcca    5100
gttaccttcg gaaaaagagt tggtagctct tgatccggca acaaaccac cgctggtagc    5160 ggtggttttt ttgtttgcaa gcagcagatt acgcgcagaa aaaaggatc tcaagaagat    5220 cctttgatct tttctacggg gtctgacgct cagtggaacg aaaactcacg ttaagggatt    5280
ttggtcatgc attctaggta ctaaaacaat tcatccagta aaatataata ttttatttc    5340 tcccaatcag gcttgatccc cagtaagtca aaaaatagct cgacatactg ttcttccccg    5400
atatcctccc tgatcgaccg gacgcagaag gcaatgtcat accacttgtc cgccctgccg    5460
cttctcccaa gatcaataaa gccacttact ttgccatctt tcacaaagat gttgctgtct    5520
cccaggtcgc cgtgggaaaa gacaagttcc tcttcgggct tttccgtctt taaaaaatca    5580
tacagctcgc gcggatcttt aaatggagtg tcttcttccc agttttcgca atccacatcg    5640
gccagatcgt tattcagtaa gtaatccaat tcggctaagc ggctgtctaa gctattcgta    5700
tagggacaat ccgatatgtc gatggagtga aagagcctga tgcactccgc atacagctcg    5760
ataatctttt cagggctttg ttcatcttca tactcttccg agcaaaggac gccatcggcc    5820
tcactcatga gcagattgct ccagccatca tgccgttcaa agtgcaggac ctttggaaca    5880
ggcagctttc cttccagcca tagcatcatg tcctttttccc gttccacatc ataggtggtc    5940
cctttatacc ggctgtccgt catttttaaa tataggtttt catttctcc caccagctta    6000 tatacccttag caggagacat tccttccgta tcttttacgc agcggtattt ttcgatcagt    6060 ttttcaatt ccggtgatat tctcatttta gccatttatt atttccttcc tctttctac    6120 agtatttaaa gataccccaa gaagctaatt ataacaagac gaactccaat tcactgttcc    6180
ttgcattcta aaaccttaaa taccagaaaa cagcttttc aaagttgttt tcaaagttgg    6240
cgtataacat agtatcgacg gagccgattt tgaaaccgcg gtgatcacag gcagcaacgc    6300
tctgtcatcg ttacaatcaa catgctaccc tccgcgagat catccgtgtt tcaaacccgg    6360
cagcttagtt gccgttcttc cgaatagcat cggtaacatg agcaaagtct gccgccttac    6420
aacggctctc ccgctgacgc cgtcccggac tgatgggctg cctgtatcga gtggtgattt    6480
tgtgccgagc tgccggtcgg ggagctgttg gctggctggt ggcaggatat attgtggtgt    6540
aaacaaattg acgcttagac aacttaataa cacattgcgg acgtttttaa tgtactgaat    6600
taacgccgaa ttaattcggg ggatctggat tttagtactg gattttggtt ttaggaatta    6660
gaaattttat tgatagaagt attttacaaa tacaaataca tactaagggt ttcttatatg    6720
ctcaacacat gagcgaaacc ctataggaac cctaattccc ttatctggga actactcaca    6780
cattattatg gagaaactcg agcttgtcga tcgacagatc cggtcggcat ctactctatt    6840
tctttgccct cggacgagtg ctggggcgtc ggtttccact atcggcgagt acttctacac    6900
```

-continued

```
agccatcggt ccagacggcc gcgcttctgc gggcgatttg tgtacgcccg acagtcccgg    6960
ctccggatcg gacgattgcg tcgcatcgac cctgcgccca agctgcatca tcgaaattgc    7020
cgtcaaccaa gctctgatag agttggtcaa gaccaatgcg gagcatatac gcccggagtc    7080
gtggcgatcc tgcaagctcc ggatgcctcc gctcgaagta gcgcgtctgc tgctccatac    7140
aagccaacca cggcctccag aagaagatgt tggcgacctc gtattgggaa tccccgaaca    7200
tcgcctcgct ccagtcaatg accgctgtta tgcggccatt gtccgtcagg acattgttgg    7260
agccgaaatc cgcgtgcacg aggtgccgga cttcggggca gtcctcggcc caaagcatca    7320
gctcatcgag agcctgcgcg acggacgcac tgacggtgtc gtccatcaca gtttgccagt    7380
gatacacatg gggatcagca atcgcgcata tgaaatcacg ccatgtagtg tattgaccga    7440
ttccttgcgg tccgaatggg ccgaacccgc tcgtctggct aagatcggcc gcagcgatcg    7500
catccatagc ctccgcgacc ggttgtagaa cagcgggcag ttcggtttca ggcaggtctt    7560
gcaacgtgac accctgtgca cggcgggaga tgcaataggt caggctctcg ctaaactccc    7620
caatgtcaag cacttccgga atcgggagcg cggccgatgc aaagtgccga taaacataac    7680
gatctttgta gaaaccatcg gcgcagctat ttacccgcag gacatatcca cgccctccta    7740
catcgaagct gaaagcacga gattcttcgc cctccgagag ctgcatcagg tcggagacgc    7800
tgtcgaactt ttcgatcaga aacttctcga cagacgtcgc ggtgagttca ggcttttttca    7860 tatctcattg ccccccccgga tctgcgaaag ctcgagagag atagatttgt agagagagac    7920
tggtgatttc agcgtgtcct ctccaaatga aatgaacttc cttatataga ggaaggtctt    7980
gcgaaggata gtgggattgt gcgtcatccc ttacgtcagt ggagatatca catcaatcca    8040
cttgctttga agacgtggtt ggaacgtctt cttttccac gatgctcctc gtgggtgggg    8100
gtccatcttt gggaccactg tcggcagagg catcttgaac gatagccttt cctttatcgc    8160
aatgatggca tttgtaggtg ccaccttcct tttctactgt ccttttgatg aagtgacaga    8220
tagctgggca atggaatccg aggaggtttc ccgatattac cctttgttga aaagtctcaa    8280
tagccctttg gtcttctgag actgtatctt tgatattctt ggagtagacg agagtgtcgt    8340
gctccaccat gttatcacat caatccactt gctttgaaga cgtggttgga acgtcttctt    8400
tttccacgat gctcctcgtg ggtggggtc catctttggg accactgtcg gcagaggcat    8460
cttgaacgat agccttttcct ttatcgcaat gatggcattt gtaggtgcca ccttcctttt    8520
ctactgtcct tttgatgaag tgacagatag ctgggcaatg gaatccgagg aggtttcccg    8580 atattccct tgttgaaaaa gtctcaatag cccttggtc ttctgagact gtatctttga    8640
tattcttgga gtagacgaga gtgtcgtgct ccaccatgtt ggcaagctgc tctagccaat    8700
acgcaaaccg cctctccccg cgcgttggcc gattcattaa tgcagctggc acgacaggtt    8760
tcccgactgg aaagcgggca gtgagcgcaa cgcaattaat gtgagttagc tcactcatta    8820
ggcaccccag gctttacact ttatgcttcc ggctcgtatg ttgtgtggaa ttgtgagcgg    8880
ataacaattt cacacaggaa acagctatga ccatgattac gaattcccttt aattaagatc    8940 tagtaacata gatgacaccg cgcgcgataa tttatcctag tttgcgcgct atattttgtt    9000
ttctatcgcg tattaaatgt ataattgcgg gactctaatc ataaaaaccc atctcataaa    9060
taacgtcatg cattacatgt taattattac atgcttaacg taattcaaca gaaattatat    9120
gataatcatc gcaagaccgg caacaggatt caatcttaag aaactttatt gccaaatgtg    9180
gtaccggttc attgtttgcc tcctgctgc ggttttttcac cgaagttcat gccagtccag    9240 cgttttttgca gcagaaaagc cgccgacttc ggtttgcggt cgcgagtgaa gatccctttc    9300
```

```
ttgttaccgc caacgcgcaa tatgccttgc gaggtcgcaa atcggcgaa attccatacc   9360
tgttcaccga cgacggcgct gacgcgatca aagacgcggt gatacatatc cagccatgca   9420
cactgatact cttcactcca catgtcggtg tacattgagt gcagcccggc taacgtatcc   9480
acgccgtatt cggtgatgat aatcggctga tgcagtttct cctgccaggc cagaagttct   9540
ttttccagta ccttctctgc cgtttccaaa tcgccgcttt ggacatacca tccgtaataa   9600
cggttcaggc acagcacatc aaagagatcg ctgatggtat cggtgtgagc gtcgcagaac   9660
attacattga cgcaggtgat cggacgcgtc gggtcgagtt tacgcgttgc ttccgccagt   9720
ggcgcgaaat attcccgtgc accttgcgga cgggtatccg gttcgttggc aatactccac   9780
atcaccacgc ttgggtggtt tttgtcacgc gctatcagct cttaatcgc ctgtaagtgc   9840
gcttgctgag tttccccgtt gactgcctct tcgctgtaca gttctttcgg cttgttgccc   9900
gcttcgaaac caatgcctaa agagaggtta agccgacag cagcagtttc atcaatcacc   9960
acgatgccat gttcatctgc ccagtcgagc atctcttcag cgtaagggta atgcgaggta  10020
cggtaggagt tggccccaat ccagtccatt aatgcgtggt cgtgcaccat cagcacgtta  10080
tcgaatcctt tgccacgcaa gtccgcatct tcatgacgac caaagccagt aaagtagaac  10140
ggtttgtggt taatcaggaa ctgttcgccc ttcactgcca ctgaccggat gccgacgcga  10200
agcgggtaga tatcacactc tgtctggctt ttggctgtga cgcacagttc atagagataa  10260
ccttcacccg gttgccagag gtgcggattc accacttgca aagtcccgct agtgccttgt  10320
ccagttgcaa ccacctgttg atccgcatca cgcagttcaa cgctgacatc accattggcc  10380
accacctgcc agtcaacaga cgcgtggtta cagtcttgcg cgacatgcgt caccacggtg  10440
atatcgtcca cccaggtgtt cggcgtggtg tagagcatta cgctgcgatg gattccggca  10500
tagttaaaga aatcatggaa gtaagactgc ttttttcttgc cgttttcgtc ggtaatcacc  10560
attcccggcg ggatagtctg ccagttcagt tcgttgttca cacaaacggt gatacgtaca  10620
cttttcccgg caataacata cggcgtgaca tcggcttcaa atggcgtata gccgccctga  10680
tgctccatca cttcctgatt attgacccac actttgccgt aatgagtgac cgcatcgaaa  10740
cgcagcacga tacgctggcc tgcccaacct ttccggtataa agacttcgcg ctgataccag  10800
acgttgcccg cataattacg aatatctgca tcggcgaact gatcgttaaa actgcctggc  10860
acagcaattg cccggctttc ttgtaacgcg ctttcccacc aacgctgatc aattccacag  10920
ttttcgcgat ccagactgaa tgcccacagg ccgtcgagtt ttttgatttc acgggttggg  10980
gtttctacag gacggacgag tcgacggttc tgtaactatc atcatcatca tagacacacg  11040
aaataaagta atcagattat cagttaaagc tatgtaatat ttacaccata accaatcaat  11100
taaaaaatag atcagtttaa agaaagatca aagctcaaaa aaataaaaag agaaagggt  11160
cctaaccaag aaaatgaagg agaaaaacta gaaatttacc ctgtagggat ccatggtccg  11220
gaccataagt atctctctcc tcgctatctc gcagctccgt ctacggcagt aatgcgact  11280
tggaggagga ggaggaggag gaggaggagg tggtggatat taatgggccg gagatgggag  11340
atggatgcgg agtggaaggg aagggaaagg tgggggaact agccggggct gtttgtgtga  11400
gtgtggctgg tggatgtcct cttcctcgcg tcaaatcacg gcggagggg agatgtatat  11460
gtacacctgc tggctgctgc ggtcgcatgg aatactggca ctctgtttca gaactggact  11520
ttattttttcc aaacattatt ttcaccggaa atctaccggg cacactgccc cttctccgat  11580
aacggcggat tacaatacct gtagcgagcc tctaagaatg tttggaggct atgtacatag  11640
```
atggggcgcg ccttaattaa ggcgcgccct gca                                    11673

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
ggctctagaa agttgttg                                                     18

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
agattcccaa agctgctg                                                     18

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
gtacatagcc tccaaaca                                                     18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
atctctctcc tcgctatc                                                     18

<210> SEQ ID NO 7
<211> LENGTH: 210
<212> TYPE: DNA
<213> ORGANISM: Lolium perenne

<400> SEQUENCE: 7
gaggctcgct acaggtattg taatccgccg ttatcggaga aggggcagtg tgcccggtag        60
atttccggtg aaaataatgt ttggaaaaat aaagtccagt tctgaaacag agtgccagta       120
ttccatgcga ccgcagcagc cagcaggtgt acatatacat ctcccccctcc gccgtgattt      180 gacgcgagaa agaggacatc caccagccac                                        210

<210> SEQ ID NO 8
<211> LENGTH: 11429
<212> TYPE: DNA
<213> ORGANISM: Artificial Sequence
<220> FEATURE:
<223> OTHER INFORMATION: Synthetic vector

<400> SEQUENCE: 8
gatccatggt ggctggtgga tgtcctcttt ctcgcgtcaa atcacggcgg agggggagat        60
gtatatgtac acctgctggc tgctgcggtc gcatggaata ctggcactct gtttcagaac      120

```
tggactttat ttttccaaac attattttca ccggaaatct accgggcaca ctgccccttc    180
tccgataacg gcggattaca atacctgtag cgagcctctg caggaattcg atatcaagct    240
tggcactggc cgtcgtttta caacgtcgtg actgggaaaa ccctggcgtt acccaactta    300
atcgccttgc agcacatccc cctttcgcca gctggcgtaa tagcgaagag gcccgcaccg    360
atcgcccttc ccaacagttg cgcagcctga atggcgaatg ctagagcagc ttgagcttgg    420
atcagattgt cgtttcccgc cttcagttta aactatcagt gtttgacagg atatattggc    480
gggtaaacct aagagaaaag agcgtttatt agaataacgg atatttaaaa gggcgtgaaa    540
aggtttatcc gttcgtccat ttgtatgtgc atgccaacca cagggttccc ctcgggatca    600
aagtactttg atccaacccc tccgctgcta tagtgcagtc ggcttctgac gttcagtgca    660
gccgtcttct gaaaacgaca tgtcgcacaa gtcctaagtt acgcgacagg ctgccgccct    720
gcccttttcc tggcgttttc ttgtcgcgtg ttttagtcgc ataaagtaga atacttgcga    780
ctagaaccgg agacattacg ccatgaacaa gagcgccgcc gctggcctgc tgggctatgc    840
ccgcgtcagc accgacgacc aggacttgac caaccaacgg gccgaactgc acgcggccgg    900
ctgcaccaag ctgttttccg agaagatcac cggcaccagg cgcgaccgcc cggagctggc    960
caggatgctt gaccacctac gccctggcga cgttgtgaca gtgaccaggc tagaccgcct   1020
ggcccgcagc acccgcgacc tactggacat tgccgagcgc atccaggagg ccggcgcggg   1080
cctgcgtagc ctggcagagc cgtgggccga caccaccacg ccggccggcc gcatggtgtt   1140
gaccgtgttc gccggcattg ccagttcga gcgttcccta atcatcgacc gcacccggag   1200
cgggcgcgag gccgccaagg cccgaggcgt gaagtttggc ccccgcccta ccctcacccc   1260
ggcacagatc gcgcacgccc gcgagctgat cgaccaggaa ggccgcaccg tgaaagaggc   1320
ggctgcactg cttggcgtgc atcgctcgac cctgtaccgc gcacttgagc gcagcgagga   1380
agtgacgccc accgaggcca ggcggcgcgg tgccttccgt gaggacgcat tgaccgaggc   1440
cgacgccctg gcggccgccg agaatgaacg ccaagaggaa caagcatgaa accgcaccag   1500
gacggccagg acgaaccgtt tttcattacc gaagagatcg aggcggagat gatcgcggcc   1560
gggtacgtgt tcgagccgcc cgcgcacgtc tcaaccgtgc ggctgcatga atcctggcc    1620 ggtttgtctg atgccaagct ggcggcctgg ccggccagct tggccgctga agaaaccgag   1680
cgccgccgtc taaaaaggtg atgtgtattt gagtaaaaca gcttgcgtca tgcggtcgct   1740
gcgtatatga tgcgatgagt aaataaacaa atacgcaagg ggaacgcatg aaggttatcg   1800
ctgtacttaa ccagaaaggc gggtcaggca agacgaccat cgcaacccat ctagcccgcg   1860
ccctgcaact cgccggggcc gatgttctgt tagtcgattc cgatcccag ggcagtgccc    1920 gcgattgggc ggcgtgcgg gaagatcaac cgctaaccgt tgtcggcatc gaccgcccga    1980
cgattgaccg cgacgtgaag gccatcggcc ggcgcgactt cgtagtgatc gacggagcgc   2040
cccaggcggc ggacttggct gtgtccgcga tcaaggcagc cgacttcgtg ctgattccgg   2100
tgcagccaag cccttacgac atatgggcca ccgccgacct ggtggagctg gttaagcagc   2160
gcattgaggt cacggatgga aggctacaag cggcctttgt cgtgtcgcgg gcgatcaaag   2220
gcacgcgcat cggcggtgag gttgccgagg cgctggccgg gtacgagctg cccattcttg   2280
agtcccgtat cacgcagcgc gtgagctacc aggcactgc cgccgccggc acaaccgttc    2340
ttgaatcaga acccgagggc gacgctgccc gcgaggtcca ggcgctggcc gctgaaatta   2400
aatcaaaact catttgagtt aatgaggtaa agagaaaatg agcaaaagca caaacacgct   2460
```

```
aagtgccggc cgtccgagcg cacgcagcag caaggctgca acgttggcca gcctggcaga    2520
cacgccagcc atgaagcggg tcaactttca gttgccggcg gaggatcaca ccaagctgaa    2580
gatgtacgcg gtacgccaag gcaagaccat taccgagctg ctatctgaat acatcgcgca    2640
gctaccagag taaatgagca aatgaataaa tgagtagatg aattttagcg gctaaaggag    2700
gcggcatgga aaatcaagaa caaccaggca ccgacgccgt ggaatgcccc atgtgtggag    2760 gaacgggcg ttggccaggc gtaagcggct gggttgtctg ccggccctgc aatggcactg    2820
gaacccccaa gcccgaggaa tcggcgtgac ggtcgcaaac catccggccc ggtacaaatc    2880
ggcgcggcgc tgggtgatga cctggtggag aagttgaagg ccgcgcaggc cgcccagcgg    2940
caacgcatcg aggcagaagc acgccccggt gaatcgtggc aagcggccgc tgatcgaatc    3000
cgcaaagaat cccggcaacc gccggcagcc ggtgcgccgt cgattaggaa gccgcccaag    3060
ggcgacgagc aaccagattt tttcgttccg atgctctatg acgtgggcac ccgcgatagt    3120
cgcagcatca tggacgtggc cgttttccgt ctgtcgaagc gtgaccgacg agctggcgag    3180
gtgatccgct acgagcttcc agacgggcac gtagaggttt ccgcagggcc ggccggcatg    3240
gccagtgtgt gggattacga cctggtactg atggcggttt cccatctaac cgaatccatg    3300
aaccgatacc gggaagggaa gggagacaag cccggccgcg tgttccgtcc acacgttgcg    3360
gacgtactca agttctgccg gcgagccgat ggcggaaagc agaaagacga cctggtagaa    3420
acctgcattc ggttaaacac cacgcacgtt gccatgcagc gtacgaagaa ggccaagaac    3480
ggccgcctgg tgacggtatc cgagggtgaa gccttgatta ccgctacaa gatcgtaaag    3540 agcgaaaccg gcggccgga gtacatcgag atcgagctag ctgattggat gtaccgcgag    3600
atcacagaag gcaagaaccc ggacgtgctg acggttcacc ccgattactt tttgatcgat    3660
cccggcatcg gccgttttct ctaccgcctg gcacgccgcg ccgcaggcaa ggcagaagcc    3720
agatggttgt tcaagacgat ctacgaacgc agtggcagcg ccggagagtt caagaagttc    3780
tgtttcaccg tgcgcaagct gatcgggtca atgacctgc ggagtacga tttgaaggag    3840 gaggcggggc aggctggccc gatcctagtc atgcgctacc gcaacctgat cgagggcgaa    3900
gcatccgccg gttcctaatg tacggagcag atgctagggc aaattgccct agcagggaa    3960 aaaggtcgaa aaggtctctt tcctgtggat agcacgtaca ttgggaaccc aaagccgtac    4020
attgggaacc ggaacccgta cattgggaac ccaaagccgt acattgggaa ccggtcacac    4080
atgtaagtga ctgatataaa agagaaaaaa ggcgattttt ccgcctaaaa ctctttaaaa    4140
cttattaaaa ctcttaaaac ccgcctggcc tgtgcataac tgtctggcca gcgcacagcc    4200
gaagagctgc aaaaagcgcc taccttcgg tcgctgcgct ccctacgccc cgccgcttcg    4260
cgtcggccta tcgcggccgc tggccgctca aaaatggctg gcctacgcc aggcaatcta    4320 ccagggcgcg acaagccgc gccgtcgcca ctcgaccgcc ggcgcccaca tcaaggcacc    4380
ctgcctcgcg cgtttcggtg atgacggtga aaacctctga cacatgcagc tcccggagac    4440
ggtcacagct tgtctgtaag cggatgccgg gagcagacaa gcccgtcagg gcgcgtcagc    4500
gggtgttggc gggtgtcggg gcgcagccat gacccagtca cgtagcgata gcggagtgta    4560
tactggctta actatgcggc atcagagcag attgtactga gagtgcacca tatgcggtgt    4620
gaaataccgc acagatgcgt aaggagaaaa taccgcatca ggcgctcttc cgcttcctcg    4680
ctcactgact cgctgcgctc ggtcgttcgg ctgcggcgag cggtatcagc tcactcaaag    4740
gcggtaatac ggttatccac agaatcaggg gataacgcag gaaagaacat gtgagcaaaa    4800
ggccagcaaa aggccaggaa ccgtaaaaag gccgcgttgc tggcgttttt ccataggctc    4860
```

```
cgcccccctg acgagcatca caaaaatcga cgctcaagtc agaggtggcg aaacccgaca    4920
ggactataaa gataccaggc gtttccccct ggaagctccc tcgtgcgctc tcctgttccg    4980
accctgccgc ttaccggata cctgtccgcc tttctccctt cgggaagcgt ggcgctttct    5040
catagctcac gctgtaggta tctcagttcg gtgtaggtcg ttcgctccaa gctgggctgt    5100
gtgcacgaac cccccgttca gcccgaccgc tgcgccttat ccggtaacta tcgtcttgag    5160
tccaacccgg taagacacga cttatcgcca ctggcagcag ccactggtaa caggattagc    5220
agagcgaggt atgtaggcgg tgctacagag ttcttgaagt ggtggcctaa ctacggctac    5280
actagaagga cagtatttgg tatctgcgct ctgctgaagc cagttacctt cggaaaaaga    5340
gttggtagct cttgatccgg caaacaaacc accgctggta gcggtggttt ttttgtttgc    5400
aagcagcaga ttacgcgcag aaaaaaagga tctcaagaag atcctttgat cttttctacg    5460
gggtctgacg ctcagtggaa cgaaaactca cgttaaggga ttttggtcat gcattctagg    5520
tactaaaaca attcatccag taaaatataa tattttattt tctcccaatc aggcttgatc    5580
cccagtaagt caaaaaatag ctcgacatac tgttcttccc cgatatcctc cctgatcgac    5640
cggacgcaga aggcaatgtc ataccacttg tccgccctgc cgcttctccc aagatcaata    5700
aagccactta ctttgccatc tttcacaaag atgttgctgt ctcccaggtc gccgtgggaa    5760
aagacaagtt cctcttcggg cttttccgtc tttaaaaaat catacagctc gcgcggatct    5820
ttaaatggag tgtcttcttc ccagttttcg caatccacat cggccagatc gttattcagt    5880
aagtaatcca attcggctaa gcggctgtct aagctattcg tatagggaca atccgatatg    5940
tcgatggagt gaaagagcct gatgcactcc gcatacagct cgataatctt ttcagggctt    6000
tgttcatctt catactcttc cgagcaaagg acgccatcgg cctcactcat gagcagattg    6060
ctccagccat catgccgttc aaagtgcagg acctttggaa caggcagctt tccttccagc    6120
catagcatca tgtccttttc ccgttccaca tcataggtgg tccctttata ccggctgtcc    6180
gtcatttttta aatataggtt ttcatttttct cccaccagct tatataccttt agcaggagac    6240
attccttccg tatcttttac gcagcggtat ttttcgatca gttttttcaa ttccggtgat    6300
attctcattt tagccattta ttatttcctt cctcttttct acagtattta agataccccc    6360
aagaagctaa ttataacaag acgaactcca attcactgtt ccttgcattc taaaacctta    6420
aataccagaa aacagctttt tcaaagttgt tttcaaagtt ggcgtataac atagtatcga    6480
cggagccgat tttgaaaccg cggtgatcac aggcagcaac gctctgtcat cgttacaatc    6540
aacatgctac cctccgcgag atcatccgtg tttcaaaccc ggcagcttag ttgccgttct    6600
tccgaatagc atcggtaaca tgagcaaagt ctgccgcctt acaacggctc tcccgctgac    6660
gccgtcccga actgatgggc tgcctgtatc gagtggtgat tttgtgccga gctgccggtc    6720
ggggagctgt tggctggctg gtggcaggat atattgtggt gtaaacaaat tgacgcttag    6780
acaacttaat aacacattgc ggacgttttt aatgtactga attaacgccg aattaattcg    6840
ggggatctgg attttagtac tggatttttgg ttttaggaat tagaaatttt attgatagaa    6900
gtatttttaca aatacaaata catactaagg gtttcttata tgctcaacac atgagcgaaa    6960
ccctatagga accctaattc ccttatctgg gaactactca cacattatta tggagaaact    7020
cgagcttgtc gatcgacaga tccggtcggc atctactcta tttctttgcc ctcggacgag    7080
tgctggggcg tcggtttcca ctatcggcga gtacttctac acagccatcg gtccagacgg    7140
ccgcgcttct gcgggcgatt tgtgtacgcc cgacagtccc ggctccggat cggacgattg    7200
```

-continued

```
cgtcgcatcg acccctgcgcc caagctgcat catcgaaatt gccgtcaacc aagctctgat    7260
agagttggtc aagaccaatg cggagcatat acgcccggag tcgtggcgat cctgcaagct    7320
ccggatgcct ccgctcgaag tagcgcgtct gctgctccat acaagccaac cacggcctcc    7380
agaagaagat gttggcgacc tcgtattggg aatccccgaa catcgcctcg ctccagtcaa    7440
tgaccgctgt tatgcggcca ttgtccgtca ggacattgtt ggagccgaaa tccgcgtgca    7500
cgaggtgccg gacttcgggg cagtcctcgg cccaaagcat cagctcatcg agagcctgcg    7560
cgacggacgc actgacggtg tcgtccatca cagtttgcca gtgatacaca tggggatcag    7620
caatcgcgca tatgaaatca cgccatgtag tgtattgacc gattccttgc ggtccgaatg    7680
ggccgaaccc gctcgtctgg ctaagatcgg ccgcagcgat cgcatccata gcctccgcga    7740
ccggttgtag aacagcgggc agttcggttt caggcaggtc ttgcaacgtg acaccctgtg    7800
cacggcggga gatgcaatag gtcaggctct cgctaaactc cccaatgtca agcacttccg    7860
gaatcgggag cgcggccgat gcaaagtgcc gataaacata acgatctttg tagaaaccat    7920
cggcgcagct atttacccgc aggacatatc cacgccctcc tacatcgaag ctgaaagcac    7980
gagattcttc gccctccgag agctgcatca ggtcggagac gctgtcgaac ttttcgatca    8040
gaaacttctc gacagacgtc gcggtgagtt caggcttttt catatctcat tgccccccg    8100 gatctgcgaa agctcgagag agatagattt gtagagagag actggtgatt tcagcgtgtc    8160
ctctccaaat gaaatgaact tccttatata gaggaaggtc ttgcgaagga tagtgggatt    8220
gtgcgtcatc ccttacgtca gtggagatat cacatcaatc cacttgcttt gaagacgtgg    8280
ttggaacgtc ttcttttttcc acgatgctcc tcgtgggtgg gggtccatct ttgggaccac    8340
tgtcggcaga ggcatcttga acgatagcct ttcctttatc gcaatgatgg catttgtagg    8400
tgccaccttc cttttctact gtccttttga tgaagtgaca gatagctggg caatggaatc    8460
cgaggaggtt tcccgatatt acccttttgtt gaaaagtctc aatagccctt tggtcttctg    8520
agactgtatc tttgatattc ttggagtaga cgagagtgtc gtgctccacc atgttatcac    8580
atcaatccac ttgctttgaa acgtggttg gaacgtcttc ttttttccacg atgctcctcg    8640 tgggtggggg tccatctttg gaccactgt cggcagaggc atcttgaacg atagcctttc    8700
ctttatcgca atgatggcat ttgtaggtgc caccttcctt ttctactgtc cttttgatga    8760
agtgacagat agctgggcaa tggaatccga ggaggtttcc cgatattacc cttttgttgaa    8820 aagtctcaat agccctttgg tcttctgaga ctgtatcttt gatattcttg gagtagacga    8880
gagtgtcgtg ctccaccatg ttggcaagct gctctagcca atacgcaaac cgcctctccc    8940
cgcgcgttgg ccgattcatt aatgcagctg gcacgacagg tttcccgact ggaaagcggg    9000
cagtgagcgc aacgcaatta atgtgagtta gctcactcat taggcacccc aggctttaca    9060
ctttatgctt ccggctcgta tgttgtgtgg aattgtgagc ggataacaat ttcacacagg    9120
aaacagctat gaccatgatt acgaattccc ttaattaaga tctagtaaca tagatgacac    9180
cgcgcgcgat aatttatcct agtttgcgcg ctatattttg ttttctatcg cgtattaaat    9240
gtataattgc gggactctaa tcataaaaac ccatctcata ataacgtca tgcattacat    9300 gttaattatt acatgcttaa cgtaattcaa cagaaattat atgataatca tcgcaagacc    9360
ggcaacagga ttcaatctta agaaacttta ttgccaaatg tggtaccggt tcattgtttg    9420
cctccctgct gcggttttttc accgaagttc atgccagtcc agcgttttg cagcagaaaa    9480 gccgccgact tcggtttgcg gtcgcgagtg aagatcccctt tcttgttacc gccaacgcgc    9540
aatatgcctt gcgaggtcgc aaaatcggcg aaattccata cctgttcacc gacgacggcg    9600
```

```
ctgacgcgat caaagacgcg gtgatacata tccagccatg cacactgata ctcttcactc    9660
cacatgtcgg tgtacattga gtgcagcccg gctaacgtat ccacgccgta ttcggtgatg    9720
ataatcggct gatgcagttt ctcctgccag gccagaagtt cttttccag taccttctct    9780
gccgtttcca aatcgccgct ttggacatac catccgtaat aacggttcag gcacagcaca    9840
tcaaagagat cgctgatggt atcggtgtga gcgtcgcaga acattacatt gacgcaggtg    9900
atcggacgcg tcgggtcgag tttacgcgtt gcttccgcca gtggcgcgaa atattcccgt    9960
gcaccttgcg gacgggtatc cggttcgttg gcaatactcc acatcaccac gcttgggtgg   10020
tttttgtcac gcgctatcag ctctttaatc gcctgtaagt gcgcttgctg agtttccccg   10080
ttgactgcct cttcgctgta cagttctttc ggcttgttgc ccgcttcgaa accaatgcct   10140
aaagagaggt taaagccgac agcagcagtt tcatcaatca ccacgatgcc atgttcatct   10200
gcccagtcga gcatctcttc agcgtaaggg taatgcgagg tacggtagga gttggcccca   10260
atccagtcca ttaatgcgtg gtcgtgcacc atcagcacgt tatcgaatcc tttgccacgc   10320
aagtccgcat cttcatgacg accaaagcca gtaaagtaga acggtttgtg gttaatcagg   10380
aactgttcgc ccttcactgc cactgaccgg atgccgacgc gaagcgggta gatatcacac   10440
tctgtctggc ttttggctgt gacgcacagt tcatagagat aaccttcacc cggttgccag   10500
aggtgcggat tcaccacttg caaagtcccg ctagtgcctt gtccagttgc aaccacctgt   10560
tgatccgcat cacgcagttc aacgctgaca tcaccattgg ccaccacctg ccagtcaaca   10620
gacgcgtggt tacagtcttg cgcgacatgc gtcaccacgg tgatatcgtc cacccaggtg   10680
ttcggcgtgg tgtagagcat tacgctgcga tggattccgg catagttaaa gaaatcatgg   10740
aagtaagact gcttttcttt gccgttttcg tcggtaatca ccattcccgg cgggatagtc   10800
tgccagttca gttcgttgtt cacacaaacg gtgatacgta cacttttccc ggcaataaca   10860
tacggcgtga catcggcttc aaatggcgta tagccgccct gatgctccat cacttcctga   10920
ttattgaccc acactttgcc gtaatgagtg accgcatcga aacgcagcac gatacgctgg   10980
cctgcccaac ctttcggtat aaagacttcg cgctgatacc agacgttgcc cgcataatta   11040
cgaatatctg catcggcgaa ctgatcgtta aaactgcctg gcacagcaat tgcccggctt   11100
tcttgtaacg cgctttccca ccaacgctga tcaattccac agttttcgcg atccagactg   11160
aatgcccaca ggccgtcgag tttttgatt tcacggttg gggttctac aggacggacg   11220
agtcgacggt tctgtaacta tcatcatcat catagacaca cgaaataaag taatcagatt   11280
atcagttaaa gctatgtaat atttacacca taaccaatca attaaaaaat agatcagttt   11340
aaagaaagat caaagctcaa aaaaataaaa agagaaaagg gtcctaacca agaaaatgaa   11400
ggagaaaaac tagaaattta ccctgtagg                                     11429
```

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
ccgttttgtc gagtttggt                                                      19

<210> SEQ ID NO 10
<211> LENGTH: 22
<212> TYPE: DNA

```
<213> ORGANISM: Artificial Sequence
<220> FEATURE:
<223> OTHER INFORMATION: Synthetic primer

<400> SEQUENCE: 10
agcaactgta accgaacata gc                                              22

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tgtagcttga tcgcataccc                                                 20

<210> SEQ ID NO 12
<211> LENGTH: 19
<212> TYPE: DNA
<213> ORGANISM: Artificial Sequence
<220> FEATURE:
<223> OTHER INFORMATION: Synthetic primer

<400> SEQUENCE: 12
actccctggt agccacctt                                                  19

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
aactcaactt gaagtgttgg agtg                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
agatctggtc ctggaaagaa tatg                                            24

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gtctcgacta cctcggcaac                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
accgaacatg gagaacatgg                                                 20
```

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
gaaactgcat cagccgatta                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
ttcaccgaag ttcatgccag                                              20

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
aatacgaggt cgccaacatc t                                            21

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
aggaacccta attcccttat ctg                                          23

<210> SEQ ID NO 21
<211> LENGTH: 785
<212> TYPE: DNA
<213> ORGANISM: Artificial Sequence
<220> FEATURE:
<223> OTHER INFORMATION: Synthetic vector

<400> SEQUENCE: 21
catggtggag cacgacactc tcgtctactc caagaatatc aaagatacag tctcagaaga      60
ccaaagggct attgagactt ttcaacaaag ggtaatatcg ggaaacctcc tcggattcca     120
ttgcccagct atctgtcact tcatcaaaag acagtagaa aaggaaggtg gcacctacaa      180
atgccatcat tgcgataaag gaaaggctat cgttcaagat gcctctgccg acagtggtcc     240
caaagatgga cccccaccca cgaggagcat cgtggaaaaa gaagacgttc caaccacgtc     300
ttcaaagcaa gtggattgat gtgataaacat ggtggagcac gacactctcg tctactccaa    360
gaatatcaaa gatacagtct cagaagacca aagggctatt gagactttt caacaaaggg      420 aatatcggga aacctcctcg gattccattg cccagctatc tgtcacttca tcaaaaggac     480
agtagaaaag gaaggtggca cctacaaatg ccatcattgc gataaaggaa aggctatcgt     540
tcaagatgcc tctgccgaca gtggtcccaa agatggaccc ccacccacga ggagcatcgt     600

-continued

| | |
|---|---|
| ggaaaaagaa gacgttccaa ccacgtcttc aaagcaagtg gattgatgtg atatctccac | 660 |
| tgacgtaagg gatgacgcac aatcccacta tccttcgcaa gaccttcctc tatataagga | 720 |
| agttcatttc atttggagag gacacgctga aatcaccagt ctctctctac aaatctatct | 780 |
| ctctc | 785 |

<210> SEQ ID NO 22
<211> LENGTH: 6129
<212> TYPE: DNA
<213> ORGANISM: Artificial Sequence
<220> FEATURE:
<223> OTHER INFORMATION: Synthetic vector

<400> SEQUENCE: 22

| | |
|---|---|
| gcgcacattt ccccgaaaag tgccacctga tgcggtgtga ataccgcac agatgcgtaa | 60 |
| ggagaaaata ccgcatcagg aaattgtaag cgttaatatt ttgttaaaat tcgcgttaaa | 120 |
| tttttgttaa atcagctcat ttttaacca ataggccgaa atcggcaaaa tcccttataa | 180 |
| atcaaaagaa tagaccgaga tagggttgag tgttgttcca gtttggaaca agagtccact | 240 |
| attaaagaac gtggactcca acgtcaaagg gcgaaaaacc gtctatcagg gcgatggccc | 300 |
| actacgtgaa ccatcaccct aatcaagttt tttggggtcg aggtgccgta aagcactaaa | 360 |
| tcggaaccct aaagggagcc cccgatttag agcttgacgg ggaaagccgg cgaacgtggc | 420 |
| gagaaaggaa gggaagaaag cgaaaggagc gggcgctagg gcgctggcaa gtgtagcggt | 480 |
| cacgctgcgc gtaaccacca cacccgccgc gcttaatgcg ccgctacagg gcgcgtccat | 540 |
| tcgccattca ggctgcgcaa ctgttgggaa gggcgatcgg tgcgggcctc ttcgctatta | 600 |
| cgccagctgg cgaaaggggg atgtgctgca aggcgattaa gttgggtaac gccagggttt | 660 |
| tcccagtcac gacgttgtaa aacgacggcc agtgaattgt aatacgactc actatagggc | 720 |
| gaattgggcc cgacgtcgca tgctcccggc cgccatggcg gccgcgggaa ttcgatttta | 780 |
| attaaggcgc gccccatcta tgagcagctt gccaacatgg tggagcacga cactctcgtc | 840 |
| tactccaaga atatcaaaga tacagtctca gaagaccaaa gggctattga acttttcaa | 900 |
| caaagggtaa tatcgggaaa cctcctcgga ttccattgcc cagctatctg tcacttcatc | 960 |
| aaaaggacag tagaaaagga aggtggcacc tacaaatgcc atcattgcga taaaggaaag | 1020 |
| gctatcgttc aagatgcctc tgccgacagt ggtcccaaag atggacccc acccacgagg | 1080 |
| agcatcgtgg aaaaagaaga cgttccaacc acgtcttcaa agcaagtgga ttgatgtgaa | 1140 |
| catggtggag cacgacactc tcgtctactc caagaatatc aaagatacag tctcagaagg | 1200 |
| ccaaagggct attgagactt tcaacaaag ggtaatatcg ggaaacctcc tcggattcca | 1260 |
| ttgcccagct atctgtcact tcatcaaaag gacagtagaa aaggaaggtg gcacctacaa | 1320 |
| atgccatcat tgcgataaag gaaaggctat cgttcaagat gctctgccga cagtggtccc | 1380 |
| aaagatggac ccccacccac gaggagcatc gtggaaaaag aagacgttcc aaccacgtct | 1440 |
| tcaaagcaag tggattgatg tgatatctcc actgacgtaa gggatgacgc acaatcccac | 1500 |
| tatccttcgc aagacccttc ctctatataa ggaagttcat ttcatttgga gggacacgc | 1560 |
| tgaaatcacc agtctctctc tacaaatcta tctctctcca ttaatggtcc ggaccatgga | 1620 |
| tccctacagg gtaaatttct agttttctc cttcattttc ttggttagga cccttttctc | 1680 |
| tttttatttt tttgagcttt gatctttctt taaactgatc tatttttaa ttgattggtt | 1740 |
| atggtgtaaa tattacatag ctttaactga taatctgatt actttattc gtgtgtctat | 1800 |
| gatgatgatg atagttacag aaccgtcgac tcgtccgtcc tgtagaaacc ccaacccgtg | 1860 |

```
aaatcaaaaa actcgacggc ctgtgggcat tcagtctgga tcgcgaaaac tgtggaattg    1920
atcagcgttg gtgggaaagc gcgttacaag aaagccgggc aattgctgtg ccaggcagtt    1980
ttaacgatca gttcgccgat gcagatattc gtaattatgc gggcaacgtc tggtatcagc    2040
gcgaagtctt tataccgaaa ggttgggcag gccagcgtat cgtgctgcgt ttcgatgcgg    2100
tcactcatta cggcaaagtg tgggtcaata atcaggaagt gatggagcat cagggcggct    2160
atacgccatt tgaagccgat gtcacgccgt atgttattgc cgggaaaagt gtacgtatca    2220
ccgtttgtgt gaacaacgaa ctgaactggc agactatccc gccgggaatg gtgattaccg    2280
acgaaaacgg caagaaaaag cagtcttact tccatgattt cttaactat gccggaatcc    2340 atcgcagcgt aatgctctac accacgccga cacctgggt ggacgatatc accgtggtga    2400
cgcatgtcgc gcaagactgt aaccacgcgt ctgttgactg gcaggtggtg gccaatggtg    2460
atgtcagcgt tgaactgcgt gatgcggatc aacaggtggt tgcaactgga caaggcacta    2520
gcgggacttt gcaagtggtg aatccgcacc tctggcaacc gggtgaaggt tatctctatg    2580
aactgtgcgt cacagccaaa agccagacag agtgtgatat ctacccgctt cgcgtcggca    2640
tccggtcagt ggcagtgaag ggcgaacagt tcctgattaa ccacaaaccg ttctacttta    2700
ctggctttgg tcgtcatgaa gatgcggact tgcgtggcaa aggattcgat aacgtgctga    2760
tggtgcacga ccacgcatta atggactgga ttggggccaa ctcctaccgt acctcgcatt    2820
acccttacgc tgaagagatg ctcgactggg cagatgaaca tggcatcgtg gtgattgatg    2880
aaactgctgc tgtcggcttt aacctctctt taggcattgg tttcgaagcg ggcaacaagc    2940
cgaaagaact gtacagcgaa gaggcagtca acggggaaac tcagcaagcg cacttacagg    3000
cgattaaaga gctgatagcg cgtgacaaaa accacccaag cgtggtgatg tggagtattg    3060
ccaacgaacc ggatacccgt ccgcaaggtg cacgggaata tttcgcgcca ctggcggaag    3120
caacgcgtaa actcgacccg acgcgtccga tcacctgcgt caatgtaatg ttctgcgacg    3180
ctcacaccga taccatcagc gatctctttg atgtgctgtg cctgaaccgt tattacggat    3240
ggtatgtcca aagcggcgat ttggaaacgg cagagaaggt actggaaaaa gaacttctgg    3300
cctggcagga gaaactgcat cagccgatta tcatcaccga atacggcgtg gatacgttag    3360
ccgggctgca ctcaatgtac accgacatgt ggagtgaaga gtatcagtgt gcatggctgg    3420
atatgtatca ccgcgtcttt gatcgcgtca gcgccgtcgt cggtgaacag gtatggaatt    3480
tcgccgattt tgcgacctcg caaggcatat tgcgcgttgg cggtaacaag aaagggatct    3540
tcactcgcga ccgcaaaccg aagtcggcgg cttttctgct gcaaaaacgc tggactggca    3600
tgaacttcgg tgaaaaaccg cagcagggag gcaaacaatg aaccggtacc acatttggca    3660
ataaagtttc ttaagattga atcctgttgc cggtcttgcg atgattatca tataatttct    3720
gttgaattac gttaagcatg taataattaa catgtaatgc atgacgttat ttatgagatg    3780 ggttttatg attagagtcc cgcaattata catttaatac gcgatagaaa acaaaatata    3840
gcgcgcaaac taggataaat tatcgcgcgc ggtgtcatct atgttactag atcttaatta    3900
aggcgcgcca atcactaggg tcgaccatat gggagagctc ccaacgcgtt ggatgcatag    3960
cttgagtatt ctatagtgtc acctaaatag cttggcgtaa tcatggtcat agctgtttcc    4020
tgtgtgaaat tgttatccgc tcacaattcc acacaacata cgagccggaa gcataaagtg    4080
taaagcctgg ggtgcctaat gagtgagcta actcacatta attgcgttgc gctcactgcc    4140
cgctttccag tcgggaaacc tgtcgtgcca gctgcattaa tgaatcggcc aacgcgcggg    4200
```

-continued

```
gagaggcggt tgcgtattg ggcgctcttc cgcttcctcg ctcactgact cgctgcgctc  4260
ggtcgttcgg ctgcggcgag cggtatcagc tcactcaaag gcggtaatac ggttatccac  4320
agaatcaggg gataacgcag gaaagaacat gtgagcaaaa ggccagcaaa aggccaggaa  4380
ccgtaaaaag gccgcgttgc tggcgttttt ccataggctc cgcccccctg acgagcatca  4440
caaaaatcga cgctcaagtc agaggtggcg aaacccgaca ggactataaa gataccaggc  4500
gtttccccct ggaagctccc tcgtgcgctc tcctgttccg accctgccgc ttaccggata  4560
cctgtccgcc tttctccctt cgggaagcgt ggcgctttct catagctcac gctgtaggta  4620
tctcagttcg gtgtaggtcg ttcgctccaa gctgggctgt gtgcacgaac cccccgttca  4680
gcccgaccgc tgcgccttat ccggtaacta tcgtcttgag tccaacccgg taagacacga  4740
cttatcgcca ctggcagcag ccactggtaa caggattagc agagcgaggt atgtaggcgg  4800
tgctacagag ttcttgaagt ggtggcctaa ctacggctac actagaagaa cagtatttgg  4860
tatctgcgct ctgctgaagc cagttacctt cggaaaaaga gttggtagct cttgatccgg  4920
caaacaaacc accgctggta gcggtggttt ttttgtttgc aagcagcaga ttacgcgcag  4980
aaaaaaagga tctcaagaag atcctttgat cttttctacg gggtctgacg ctcagtggaa  5040
cgaaaactca cgttaaggga ttttggtcat gagattatca aaaaggatct tcacctagat  5100
ccttttaaat taaaaatgaa gttttaaatc aatctaaagt atatatgagt aaacttggtc  5160
tgacagttac caatgcttaa tcagtgaggc acctatctca gcgatctgtc tatttcgttc  5220
atccatagtt gcctgactcc ccgtcgtgta gataactacg atacgggagg gcttaccatc  5280
tggccccagt gctgcaatga taccgcgaga cccacgctca ccggctccag atttatcagc  5340
aataaaccag ccagccggaa gggccgagcg cagaagtggt cctgcaactt tatccgcctc  5400
catccagtct attaattgtt gccgggaagc tagagtaagt agttcgccag ttaatagttt  5460
gcgcaacgtt gttgccattg ctacaggcat cgtggtgtca cgctcgtcgt ttggtatggc  5520
ttcattcagc tccggttccc aacgatcaag gcgagttaca tgatccccca tgttgtgcaa  5580
aaaagcggtt agctccttcg gtcctccgat cgttgtcaga agtaagttgg ccgcagtgtt  5640
atcactcatg gttatggcag cactgcataa ttctcttact gtcatgccat ccgtaagatg  5700
cttttctgtg actggtgagt actcaaccaa gtcattctga gaatagtgta tgcggcgacc  5760
gagttgctct tgcccggcgt caatacggga taataccgcg ccacatagca gaactttaaa  5820
agtgctcatc attggaaaac gttcttcggg gcgaaaactc tcaaggatct taccgctgtt  5880
gagatccagt tcgatgtaac ccactcgtgc acccaactga tcttcagcat cttttacttt  5940
caccagcgtt tctgggtgag caaaaacagg aaggcaaaat gccgcaaaaa agggaataag  6000
ggcgacacgg aaatgttgaa tactcatact cttcctttt caatattatt gaagcattta  6060
tcagggttat tgtctcatga gcggatacat atttgaatgt atttagaaaa ataaacaaat  6120
aggggttcc                                                           6129
```